United States Patent
Zilberstein et al.

(10) Patent No.: US 8,492,725 B2
(45) Date of Patent: Jul. 23, 2013

(54) METHOD AND SYSTEM OF OPTIMIZED VOLUMETRIC IMAGING

(71) Applicant: Spectrum Dynamics LLC, Orangeburg, NY (US)

(72) Inventors: Yoel Zilberstein, Herzlia (IL); Nathaniel Roth, Herzlia Pituach (IL); Benny Rousso, Rishon-LeZion (IL); Shlomo Ben-Haim, Orangeburg, NY (US)

(73) Assignee: Biosensors International Group Ltd., Hamilton (BM)

( * ) Notice: Subject to any disclaimer, the term of this patent is extended or adjusted under 35 U.S.C. 154(b) by 0 days.

(21) Appl. No.: 13/726,316

(22) Filed: Dec. 24, 2012

(65) Prior Publication Data

US 2013/0114792 A1 May 9, 2013

Related U.S. Application Data

(63) Continuation of application No. 12/792,856, filed on Jun. 3, 2010, now Pat. No. 8,338,788.

(60) Provisional application No. 61/229,549, filed on Jul. 29, 2009.

(51) Int. Cl.
*G01T 1/166* (2006.01)

(52) U.S. Cl.
USPC .................................................. 250/363.04

(58) Field of Classification Search
USPC .................... 250/362, 363.01–363.1
See application file for complete search history.

(56) References Cited

U.S. PATENT DOCUMENTS

| 630,611 | A | 8/1899 | Knapp et al. |
| 2,776,377 | A | 1/1957 | Anger |
| 3,340,866 | A | 9/1967 | Noeller |
| 3,446,965 | A | 5/1969 | Ogier et al. |
| 3,535,085 | A | 10/1970 | Shumate et al. |
| 3,684,887 | A | 8/1972 | Hugonin |
| 3,690,309 | A | 9/1972 | Pluzhnikov et al. |
| 3,719,183 | A | 3/1973 | Schwartz |
| 3,739,279 | A | 6/1973 | Hollis |
| 3,971,362 | A | 7/1976 | Pope et al. |

(Continued)

FOREIGN PATENT DOCUMENTS

| DE | 1516429 | 12/1969 |
| DE | 19814199 | 10/1999 |

(Continued)

OTHER PUBLICATIONS

Applicant-Initiated Interview Summary Dated Jan. 28, 2013 From the US Patent and Trademark Office Re.: U.S. Appl. No. 11/798,017.

(Continued)

*Primary Examiner* — Kiho Kim

(57) ABSTRACT

A system of performing a volumetric scan. The system comprises a surface of positioning a patient in a space parallel thereto, a plurality of extendable detector arms each the detector arm having a detection unit having at least one radiation detector, and an actuator which moves the detection unit along a linear path, and a gantry which supports the plurality of extendable detector arms around the surface so that each the linear path of each respective the extendable detector arm being directed toward the space.

25 Claims, 14 Drawing Sheets

U.S. PATENT DOCUMENTS

| | | |
|---|---|---|
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hogrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Comacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misic et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |

| | | | | | | |
|---|---|---|---|---|---|---|
| 5,716,595 | A | 2/1998 | Goldenberg | RE36,648 | E | 4/2000 | Uber, III et al. |
| 5,727,554 | A | 3/1998 | Kalend et al. | 6,046,454 | A | 4/2000 | Lingren et al. |
| 5,729,129 | A | 3/1998 | Acker | 6,048,334 | A | 4/2000 | Hirschman et al. |
| 5,732,704 | A | 3/1998 | Thurston et al. | 6,052,618 | A | 4/2000 | Dahlke et al. |
| 5,739,508 | A | 4/1998 | Uber, III | 6,055,450 | A | 4/2000 | Ashburn |
| 5,741,232 | A | 4/1998 | Reilly et al. | 6,055,452 | A | 4/2000 | Pearlman |
| 5,742,060 | A | 4/1998 | Ashburn | RE36,693 | E | 5/2000 | Reich |
| 5,744,805 | A | 4/1998 | Raylman et al. | 6,063,052 | A | 5/2000 | Uber et al. |
| 5,757,006 | A | 5/1998 | De Vito et al. | D426,891 | S | 6/2000 | Beale et al. |
| 5,779,675 | A | 7/1998 | Reilly et al. | D426,892 | S | 6/2000 | Beale et al. |
| 5,780,855 | A | 7/1998 | Pare et al. | 6,072,177 | A | 6/2000 | McCroskey et al. |
| 5,781,442 | A | 7/1998 | Engleson et al. | 6,076,009 | A | 6/2000 | Raylman et al. |
| 5,784,432 | A | 7/1998 | Kurtz et al. | 6,080,984 | A | 6/2000 | Friesenhahn |
| 5,786,597 | A | 7/1998 | Lingren et al. | D428,491 | S | 7/2000 | Beale et al. |
| 5,795,333 | A | 8/1998 | Reilly et al. | 6,082,366 | A | 7/2000 | Andra et al. |
| 5,800,355 | A | 9/1998 | Hasegawa | 6,090,064 | A | 7/2000 | Reilly et al. |
| 5,803,914 | A | 9/1998 | Ryals et al. | 6,091,070 | A | 7/2000 | Lingren et al. |
| 5,806,519 | A | 9/1998 | Evans, III et al. | 6,096,011 | A | 8/2000 | Trombley, III et al. |
| 5,808,203 | A | 9/1998 | Nolan, Jr. et al. | 6,107,102 | A | 8/2000 | Ferrari |
| 5,810,742 | A | 9/1998 | Pearlman | 6,115,635 | A | 9/2000 | Bourgeois |
| 5,811,814 | A | 9/1998 | Leone et al. | 6,129,670 | A | 10/2000 | Burdette et al. |
| 5,813,985 | A | 9/1998 | Carroll | 6,132,372 | A | 10/2000 | Essen-Moller |
| 5,818,050 | A | 10/1998 | Dilmanian et al. | 6,135,955 | A | 10/2000 | Madden et al. |
| 5,821,541 | A | 10/1998 | Tumer | 6,135,968 | A | 10/2000 | Brounstein |
| 5,825,031 | A | 10/1998 | Wong et al. | 6,137,109 | A | 10/2000 | Hayes |
| 5,827,219 | A | 10/1998 | Uber, III et al. | 6,145,277 | A | 11/2000 | Lawecki et al. |
| 5,828,073 | A | 10/1998 | Zhu et al. | 6,147,352 | A | 11/2000 | Ashburn |
| 5,833,603 | A | 11/1998 | Kovacs et al. | 6,147,353 | A | 11/2000 | Gagnon et al. |
| 5,838,009 | A | 11/1998 | Plummer et al. | 6,148,229 | A | 11/2000 | Morris, Sr. et al. |
| 5,840,026 | A | 11/1998 | Uber, III et al. | 6,149,627 | A | 11/2000 | Uber, III |
| 5,841,141 | A | 11/1998 | Gullberg et al. | 6,155,485 | A | 12/2000 | Coughlin et al. |
| 5,842,977 | A | 12/1998 | Lesho et al. | 6,160,398 | A | 12/2000 | Walsh |
| 5,843,037 | A | 12/1998 | Uber, III | 6,162,198 | A | 12/2000 | Coffey et al. |
| 5,846,513 | A | 12/1998 | Carroll et al. | 6,172,362 | B1 | 1/2001 | Lingren et al. |
| 5,847,396 | A | 12/1998 | Lingren et al. | 6,173,201 | B1 | 1/2001 | Front |
| 5,857,463 | A | 1/1999 | Thurston et al. | 6,184,530 | B1 | 2/2001 | Hines et al. |
| 5,871,013 | A | 2/1999 | Wainer et al. | 6,189,195 | B1 | 2/2001 | Reilly et al. |
| 5,873,861 | A | 2/1999 | Hitchins et al. | 6,194,715 | B1 | 2/2001 | Lingren et al. |
| 5,880,475 | A | 3/1999 | Oka et al. | 6,194,725 | B1 | 2/2001 | Colsher et al. |
| 5,882,338 | A | 3/1999 | Gray | 6,194,726 | B1 | 2/2001 | Pi et al. |
| 5,884,457 | A | 3/1999 | Ortiz et al. | 6,197,000 | B1 | 3/2001 | Reilly et al. |
| 5,885,216 | A | 3/1999 | Evans, III et al. | 6,202,923 | B1 | 3/2001 | Boyer et al. |
| 5,891,030 | A | 4/1999 | Johnson et al. | 6,203,775 | B1 | 3/2001 | Torchilin et al. |
| 5,893,397 | A | 4/1999 | Peterson et al. | 6,205,347 | B1 | 3/2001 | Morgan et al. |
| 5,899,885 | A | 5/1999 | Reilly et al. | 6,212,423 | B1 | 4/2001 | Krakovitz |
| 5,900,533 | A | 5/1999 | Chou | 6,223,065 | B1 | 4/2001 | Misic et al. |
| 5,903,008 | A | 5/1999 | Li | 6,224,577 | B1 | 5/2001 | Dedola et al. |
| 5,910,112 | A | 6/1999 | Judd et al. | 6,226,350 | B1 | 5/2001 | Hsieh |
| 5,911,252 | A | 6/1999 | Cassel | 6,229,145 | B1 | 5/2001 | Weinberg |
| 5,916,167 | A | 6/1999 | Kramer et al. | 6,232,605 | B1 | 5/2001 | Soluri et al. |
| 5,916,197 | A | 6/1999 | Reilly et al. | 6,233,304 | B1 | 5/2001 | Hu et al. |
| 5,920,054 | A | 7/1999 | Uber, III | 6,236,050 | B1 | 5/2001 | Tumer |
| 5,927,351 | A | 7/1999 | Zhu et al. | 6,236,878 | B1 | 5/2001 | Taylor et al. |
| 5,928,150 | A | 7/1999 | Call | 6,236,880 | B1 | 5/2001 | Raylman et al. |
| 5,932,879 | A | 8/1999 | Raylman et al. | 6,239,438 | B1 | 5/2001 | Schubert |
| 5,938,639 | A | 8/1999 | Reilly et al. | 6,240,312 | B1 | 5/2001 | Alfano et al. |
| 5,939,724 | A | 8/1999 | Eisen et al. | 6,241,708 | B1 | 6/2001 | Reilly et al. |
| 5,944,190 | A | 8/1999 | Edelen | 6,242,743 | B1 | 6/2001 | DeVito |
| 5,944,694 | A | 8/1999 | Hitchins et al. | 6,242,744 | B1 | 6/2001 | Soluri et al. |
| 5,947,935 | A | 9/1999 | Rhinehart et al. | 6,242,745 | B1 | 6/2001 | Berlad et al. |
| 5,953,884 | A | 9/1999 | Lawecki et al. | 6,246,901 | B1 | 6/2001 | Benaron |
| 5,954,668 | A | 9/1999 | Uber, III et al. | 6,252,924 | B1 | 6/2001 | Davantes et al. |
| 5,961,457 | A | 10/1999 | Raylman et al. | 6,258,576 | B1 | 7/2001 | Richards-Kortum et al. |
| 5,967,983 | A | 10/1999 | Ashburn | 6,259,095 | B1 | 7/2001 | Bouton et al. |
| 5,973,598 | A | 10/1999 | Beigel | 6,261,562 | B1 | 7/2001 | Xu et al. |
| 5,974,165 | A | 10/1999 | Giger et al. | 6,263,229 | B1 | 7/2001 | Atalar et al. |
| 5,984,860 | A | 11/1999 | Shan | 6,269,340 | B1 | 7/2001 | Ford et al. |
| 5,987,350 | A | 11/1999 | Thurston | 6,270,463 | B1 | 8/2001 | Morris, Sr. et al. |
| 5,993,378 | A | 11/1999 | Lemelson | 6,271,524 | B1 | 8/2001 | Wainer et al. |
| 5,997,502 | A | 12/1999 | Reilly et al. | 6,271,525 | B1 | 8/2001 | Majewski et al. |
| 6,002,134 | A | 12/1999 | Lingren | 6,280,704 | B1 | 8/2001 | Schutt et al. |
| 6,002,480 | A | 12/1999 | Izatt et al. | 6,281,505 | B1 | 8/2001 | Hines et al. |
| 6,017,330 | A | 1/2000 | Hitchins et al. | 6,308,097 | B1 | 10/2001 | Pearlman |
| 6,019,745 | A | 2/2000 | Gray | 6,310,968 | B1 | 10/2001 | Hawkins et al. |
| 6,021,341 | A | 2/2000 | Scibilia et al. | 6,315,981 | B1 | 11/2001 | Unger |
| 6,026,317 | A | 2/2000 | Verani | 6,317,623 | B1 | 11/2001 | Griffiths et al. |
| 6,037,595 | A | 3/2000 | Lingren | 6,317,648 | B1 | 11/2001 | Sleep et al. |
| 6,040,697 | A | 3/2000 | Misic | 6,318,630 | B1 | 11/2001 | Coughlin et al. |
| 6,042,565 | A | 3/2000 | Hirschman et al. | 6,322,535 | B1 | 11/2001 | Hitchins et al. |

| Patent No. | Date | Inventor |
|---|---|---|
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tumer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,906,330 B2 | 6/2005 | Blevis et al. |
| D507,832 S | 7/2005 | Yanniello et al. |

| | | |
|---|---|---|
| 6,915,170 B2 | 7/2005 | Engleson et al. |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Tumer |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charron et al. |
| 7,470,896 B2 | 12/2008 | Pawlak et al. |
| 7,490,085 B2 | 2/2009 | Walker et al. |
| 7,502,499 B2 | 3/2009 | Grady |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,672,491 B2 | 3/2010 | Krishnan et al. |
| 7,680,240 B2 | 3/2010 | Manjeshwar et al. |
| 7,705,316 B2 | 4/2010 | Rousso et al. |
| 7,734,331 B2 | 6/2010 | Dhawale et al. |
| 7,826,889 B2 | 11/2010 | David et al. |
| 7,831,024 B2 | 11/2010 | Metzler et al. |
| 7,835,927 B2 | 11/2010 | Schlotterbeck et al. |
| 7,872,235 B2 | 1/2011 | Rousso et al. |
| 7,894,650 B2 | 2/2011 | Weng et al. |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,204,500 B2 | 6/2012 | Weintraub et al. |
| 8,338,788 B2 | 12/2012 | Zilberstein et al. |
| 2001/0016029 A1 | 8/2001 | Tumer |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 | 11/2002 | Kaushikkar et al. |
| 2002/0168317 A1 | 11/2002 | Daighighian et al. |
| 2002/0172405 A1 | 11/2002 | Schultz |
| 2002/0179843 A1 | 12/2002 | Tanaka et al. |
| 2002/0183645 A1 | 12/2002 | Nachaliel |
| 2002/0188197 A1 | 12/2002 | Bishop et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Tumer |
| 2003/0013950 A1 | 1/2003 | Rollo et al. |
| 2003/0013966 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0135388 A1 | 7/2003 | Martucci et al. |
| 2003/0136912 A1 | 7/2003 | Juni |
| 2003/0144322 A1 | 7/2003 | Kozikowski et al. |
| 2003/0147887 A1 | 8/2003 | Wang et al. |
| 2003/0158481 A1 | 8/2003 | Stotzka et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 | 11/2003 | Tanaka |
| 2003/0215124 A1 | 11/2003 | Li |
| 2003/0216631 A1 | 11/2003 | Bloch et al. |
| 2003/0219149 A1 | 11/2003 | Vailaya et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0021065 A1 | 2/2004 | Weber |
| 2004/0044282 A1 | 3/2004 | Mixon et al. |
| 2004/0051368 A1 | 3/2004 | Caputo et al. |
| 2004/0054248 A1 | 3/2004 | Kimchy et al. |
| 2004/0054278 A1 | 3/2004 | Kimchy et al. |
| 2004/0065838 A1 | 4/2004 | Tumer |
| 2004/0075058 A1 | 4/2004 | Blevis et al. |
| 2004/0081623 A1 | 4/2004 | Eriksen et al. |
| 2004/0082918 A1 | 4/2004 | Evans et al. |
| 2004/0084340 A1 | 5/2004 | Morelle et al. |
| 2004/0086437 A1 | 5/2004 | Jackson et al. |
| 2004/0101176 A1 | 5/2004 | Mendonca et al. |
| 2004/0101177 A1 | 5/2004 | Zahlmann et al. |
| 2004/0116807 A1 | 6/2004 | Amrami et al. |
| 2004/0120557 A1 | 6/2004 | Sabol |
| 2004/0122311 A1 | 6/2004 | Cosman |
| 2004/0125918 A1 | 7/2004 | Shanmugaval et al. |
| 2004/0138557 A1 | 7/2004 | Le et al. |
| 2004/0143449 A1 | 7/2004 | Behrenbruch et al. |
| 2004/0144925 A1 | 7/2004 | Stoddart et al. |
| 2004/0153128 A1 | 8/2004 | Suresh et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |
| 2004/0195512 A1* | 10/2004 | Crosetto ................ 250/363.04 |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2004/0263865 A1 | 12/2004 | Pawlak et al. |
| 2005/0001170 A1 | 1/2005 | Juni |
| 2005/0006589 A1 | 1/2005 | Young et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |

| | | | | | | |
|---|---|---|---|---|---|---|
| 2005/0033157 | A1 | 2/2005 | Klein et al. | 2010/0140483 A1 | 6/2010 | Rousso et al. |
| 2005/0049487 | A1 | 3/2005 | Johnson et al. | 2010/0202664 A1 | 8/2010 | Busch et al. |
| 2005/0055174 | A1 | 3/2005 | David et al. | 2010/0245354 A1 | 9/2010 | Rousso et al. |
| 2005/0056788 | A1 | 3/2005 | Juni | 2012/0106820 A1 | 5/2012 | Rousso et al. |
| 2005/0074402 | A1 | 4/2005 | Cagnolini et al. | 2012/0172699 A1 | 7/2012 | Nagler et al. |
| 2005/0107698 | A1 | 5/2005 | Powers et al. | | | |
| 2005/0107914 | A1 | 5/2005 | Engleson et al. | | | |
| 2005/0108044 | A1 | 5/2005 | Koster | | | |
| 2005/0113945 | A1 | 5/2005 | Engleson et al. | | | |
| 2005/0121505 | A1 | 6/2005 | Metz et al. | | | |
| 2005/0131270 | A1 | 6/2005 | Weil et al. | | | |
| 2005/0145797 | A1 | 7/2005 | Oaknin et al. | | | |
| 2005/0148869 | A1 | 7/2005 | Masuda | | | |
| 2005/0149350 | A1 | 7/2005 | Kerr et al. | | | |
| 2005/0156115 | A1 | 7/2005 | Kobayashi et al. | | | |
| 2005/0173643 | A1 | 8/2005 | Tumer | | | |
| 2005/0187465 | A1 | 8/2005 | Motomura et al. | | | |
| 2005/0198800 | A1 | 9/2005 | Reich | | | |
| 2005/0203389 | A1 | 9/2005 | Williams | | | |
| 2005/0205792 | A1 | 9/2005 | Rousso et al. | | | |
| 2005/0205796 | A1 | 9/2005 | Bryman | | | |
| 2005/0211909 | A1 | 9/2005 | Smith | | | |
| 2005/0215889 | A1 | 9/2005 | Patterson, II | | | |
| 2005/0234424 | A1 | 10/2005 | Besing et al. | | | |
| 2005/0247893 | A1 | 11/2005 | Fu et al. | | | |
| 2005/0253073 | A1 | 11/2005 | Joram et al. | | | |
| 2005/0261936 | A1 | 11/2005 | Silverbrook et al. | | | |
| 2005/0261937 | A1 | 11/2005 | Silverbrook et al. | | | |
| 2005/0261938 | A1 | 11/2005 | Silverbrook et al. | | | |
| 2005/0266074 | A1 | 12/2005 | Zilberstein et al. | | | |
| 2005/0277833 | A1 | 12/2005 | Williams, Jr. | | | |
| 2005/0277911 | A1 | 12/2005 | Stewart et al. | | | |
| 2005/0278066 | A1 | 12/2005 | Graves et al. | | | |
| 2005/0288869 | A1 | 12/2005 | Kroll et al. | | | |
| 2006/0000983 | A1 | 1/2006 | Charron et al. | | | |
| 2006/0033028 | A1 | 2/2006 | Juni | | | |
| 2006/0036157 | A1 | 2/2006 | Tumer | | | |
| 2006/0072799 | A1 | 4/2006 | McLain | | | |
| 2006/0074290 | A1 | 4/2006 | Chen et al. | | | |
| 2006/0109950 | A1 | 5/2006 | Arenson et al. | | | |
| 2006/0122503 | A1 | 6/2006 | Burbank et al. | | | |
| 2006/0145081 | A1 | 7/2006 | Hawman | | | |
| 2006/0160157 | A1 | 7/2006 | Zuckerman | | | |
| 2006/0214097 | A1 | 9/2006 | Wang et al. | | | |
| 2006/0237652 | A1 | 10/2006 | Kimchy et al. | | | |
| 2006/0257012 | A1 | 11/2006 | Kaufman et al. | | | |
| 2007/0116170 | A1 | 5/2007 | De Man et al. | | | |
| 2007/0133852 | A1 | 6/2007 | Collins et al. | | | |
| 2007/0156047 | A1 | 7/2007 | Nagler et al. | | | |
| 2007/0166227 | A1 | 7/2007 | Liu et al. | | | |
| 2007/0189436 | A1 | 8/2007 | Goto et al. | | | |
| 2007/0194241 | A1 | 8/2007 | Rousso et al. | | | |
| 2007/0265230 | A1 | 11/2007 | Rousso et al. | | | |
| 2008/0001090 | A1 | 1/2008 | Ben-Haim et al. | | | |
| 2008/0029704 | A1 | 2/2008 | Hefetz et al. | | | |
| 2008/0033291 | A1 | 2/2008 | Rousso et al. | | | |
| 2008/0036882 | A1 | 2/2008 | Uemura et al. | | | |
| 2008/0042067 | A1 | 2/2008 | Rousso et al. | | | |
| 2008/0128626 | A1 | 6/2008 | Rousso et al. | | | |
| 2008/0137938 | A1 | 6/2008 | Zahniser | | | |
| 2008/0230702 | A1 | 9/2008 | Rousso et al. | | | |
| 2008/0230705 | A1 | 9/2008 | Rousso et al. | | | |
| 2008/0237482 | A1 | 10/2008 | Shahar et al. | | | |
| 2008/0260228 | A1 | 10/2008 | Dichterman et al. | | | |
| 2008/0260637 | A1 | 10/2008 | Dickman | | | |
| 2008/0277591 | A1 | 11/2008 | Shahar et al. | | | |
| 2009/0001273 | A1 | 1/2009 | Hawman | | | |
| 2009/0018412 | A1 | 1/2009 | Schmitt | | | |
| 2009/0078875 | A1 | 3/2009 | Rousso et al. | | | |
| 2009/0112086 | A1 | 4/2009 | Melman | | | |
| 2009/0152471 | A1 | 6/2009 | Rousso et al. | | | |
| 2009/0190807 | A1 | 7/2009 | Rousso et al. | | | |
| 2009/0201291 | A1 | 8/2009 | Ziv et al. | | | |
| 2009/0236532 | A1 | 9/2009 | Frach et al. | | | |
| 2009/0304582 | A1 | 12/2009 | Rousso et al. | | | |
| 2010/0006770 | A1 | 1/2010 | Balakin | | | |
| 2010/0021378 | A1 | 1/2010 | Rousso et al. | | | |
| 2010/0102242 | A1 | 4/2010 | Burr et al. | | | |
| 2010/0121184 | A1 | 5/2010 | Dhawale et al. | | | |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 06-109848 | 4/1994 |
| JP | 07-059763 | 3/1995 |
| JP | 07-141523 | 6/1995 |
| JP | 08-292268 | 11/1996 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Official Action Dated Feb. 7, 2013 From the US Patent and Trademark Office Re. U.S. Appl. No. 11/980,653.

Official Action Dated Dec. 19, 2012 From the US Patent and Trademark Office Re. U.s. Appl. No. 12/448,473.

Advisory Action Before the Filing of an Appeal Brief Dated Jul. 12, 2012 From the US Patent and Trademark Office Re. U.S. Appl. No. 11/667,793.

Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.

Appeal Brief Dated Jan. 19, 2010 to Notice of Appeal of Nov. 16, 2009 From the US Patent and Trademark Office Re.: U.S. Appl. No. 10/616,301.
Communication Pursuant to Article 93(3) EPC Dated Mar. 8, 2010 From the European Patent Office Re.: Application No. 06832278.3.
Communication Pursuant to Article 94(3) EPC Dated Mar. 2, 2011 From the European Patent Office Re.: Application No. 06756259.5.
Communication Pursuant to Article 94(3) EPC Dated Mar. 8, 2010 From the European Patent Office Re.: Application No. 06832278.3.
Communication Pursuant to Article 94(3) EPC Dated Jun. 11, 2012 From the European Patent Office Re.: Application No. 06756259.5.
Communication Pursuant to Article 94(3) EPC Dated May 12, 2010 From the European Patent Office Re. Application No. 06809851.6.
Communication Pursuant to Article 94(3) EPC Dated May 12, 2010 From the European Patent Office Re.: Application No. 06809851.6.
Communication Pursuant to Article 94(3) EPC Dated Nov. 12, 2012 From the European Patent Office Re. Application No. 06756258.7.
Communication Pursuant to Article 94(3) EPC Dated Apr. 16, 2010 From the European Patent Office Re. Application No. 01951883.6.
Communication Pursuant to Article 94(3) EPC Dated Sep. 17, 2012 From the European Patent Office Re. Application No. 06832278.3.
Communication Pursuant to Article 94(3) EPC Dated Nov. 18, 2011 From the European Patent Office Re. Application No. 05803689.8.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 94(3) EPC Dated Sep. 22, 2011 From the European Patent Office Re. Application No. 06756258.7.
Communication Pursuant to Article 94(3) EPC Dated Sep. 23, 2011 From the European Patent Office Re.: Application No. 06832278.3.
Communication Pursuant to Article 94(3) EPC Dated Oct. 26, 2012 From the European Patent Office Re. Application No. 05803689.8.
Communication Pursuant to Article 94(3) EPC Dated May 29, 2012 From the European Patent Office Re. Application No. 05803689.8.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Pursuant to Rules 70(2) and 70a(2) EPC Dated Apr. 4, 2011 From the European Patent Office Re. Application No. 05803689.8.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
Communication Under Rule 71(3) EPC Dated May 30, 2012 From the European Patent Office Re.: Application No. 02716285.8.
Examination Report Dated Jun. 22, 2011 From the Government of India, Patent Office, Intellectual Property Building Re. Application No. 2963/CHENP/2006.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 10, 2006 From the International Searching Authority of the Patent Cooperation Treaty Re.: Application No. PCT/IL06/00059.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 1, 2008 From the International Searching Authority Re. Application No. PCT/IL2006/000834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Jul. 2, 2007 From the International Searching Authority Re. Application No. PCT/IL2006/001291.
International Search Report Dated Aug. 3, 2006 From the International Searching Authority of the Patent Cooperation Treaty Re.: Application No. PCT/IL05/001173.
International Search Report Dated Aug. 3, 2006 From the International Searching Authority Re. Application No. PCT/IL2005/001173.
International Search Report Dated Jul. 11, 2008 From the International Searching Authority of the Patent Cooperation Treaty Re.: Application No. PCT/IL06/01511.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re. Application No. PCT/2007/000918.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.

International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Interview Summary Dated Mar. 25, 2011 From the US Patent and Trademark Office Re.: U.S. Appl. No. 10/836,223.
Interview Summary Dated May 31, 2011 From the US Patent and Trademark Office Re. U.S. Appl. No. 10/616,301.
Invitation to Pay Additional Fees Dated Jul. 10, 2008 From the International Searching Authority Re. : Application No. PCT/IL06/01511.
Invitation to Pay Additional Fees Dated Feb. 15, 2007 From the International Searching Authority Re.: Application No. PCT/IL05/00575.
Notice of Allowance Dated Feb. 2, 2012 From the US Patent and Trademark Office Re. U.S. Appl. No. 11/628,074.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Notice of Allowance Dated Oct. 11, 2011 From the US Patent and Trademark Office Re. U.S. Appl. No. 11/988,926.
Notice of Allowance Dated Nov. 15, 2010 From the US Patent and Trademark Office Re. U.S. Appl. No. 10/616,301.
Notice of Allowance Dated Nov. 15, 2012 From the US Patent and Trademark Office Re.: U.S. Appl. No. 11/980,683.
Notice of Allowance Dated Jul. 16, 2009 From the US Patent and Trademark Office Re.: U.S. Appl. No. 12/084,559.
Notice of Allowance Dated Sep. 16, 2011 From the US Patent and Trademark Office Re.: U.S. Appl. No. 11/607,075.
Notice of Allowance Dated Dec. 17, 2010 From the US Patent and Trademark Office Re. U.S. Appl. No. 11/980,617.
Notice of Allowance Dated Sep. 17, 2009 From the US Patent and Trademark Office Re.: U.S. Appl. No. 10/533,568. Suppl. IDS VIII in 25855.
Notice of Allowance Dated Jul. 22, 2010 From the US Patent and Trademark Office Re.: U.S. Appl. No. 11/794,799.
Notice of Allowance Dated Feb. 23, 2011 From the US Patent and Trademark Office Re.: U.S. Appl. No. 12/728,383.
Notice of Allowance Dated Jun. 23, 2011 From the US Patent and Trademark Office Re. : U.S. Appl. No. 10/616,301.
Notice of Allowance Dated Nov. 23, 2009 From the US Patent and Trademark Office Re.: U.S. Appl. No. 12/084,559.
Notice of Allowance Dated Aug. 25, 2010 From the US Patent and Trademark Office Re. U.S. Appl. No. 11/980,617.
Notice of Allowance Dated Dec. 26, 2012 From the US Patent and Trademark Office Re.: U.S. Appl. No. 11/980,690.
Notice of Allowance Dated Oct. 26, 2012 From the US Patent and Trademark Office Re. U.S. Appl. No. 12/514,785.
Notice of Allowance Dated Sep. 28, 2012 From the US Patent and Trademark Office Re. U.S. Appl. No. 12/792,856.
Notice of Allowance Dated Jun. 30, 2010 From the United States Patent and Trademark Office Re.: U.S. Appl. No. 09/727,464.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Notice of Non-Compliant Amendment Dated Feb. 14, 2011 From the US Patent and Trademark Office Re.: U.S. Appl. No. 10/616,307.
Notice of Panel Decision From Pre-Appeal Brief Review Dated Feb. 29, 2012 From the US Patent and Trademark Office Re.: U.S. Appl. No. 10/836,223.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323 and Its Translation Into English.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Mar. 1, 2012 From the US Patent and Trademark Office Re.: U.S. Appl. No. 10/616,307.
Official Action Dated Nov. 1, 2010 From the US Patent and Trademark Office Re. U.S. Appl. No. 12/728,383.
Official Action Dated Nov. 1, 2010 From the US Patent and Trademark Office Re.: U.S. Appl. No. 12/728,383.
Official Action Dated Sep. 1, 2009 From the US Patent and Trademark Office Re.: U.S. Appl. No. 11/794,799.
Official Action Dated Aug. 2, 2012 From the US Patent and Trademark Office Re. U.S. Appl. No. 12/087,150.
Official Action Dated Jul. 2, 2004 From the US Patent and Trademark Office Re.: U.S. Appl. No. 09/641,973.
Official Action Dated Mar. 2, 2010 From the US Patent and Trademark Office Re. U.S. Appl. No. 11/980,617.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Aug. 3, 2010 From the US Patent and Trademark Office Re.: U.S. Appl. No. 11/980,690.
Official Action Dated May 3, 2007 From the US Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Mar. 6, 2012 From the US Patent and Trademark Office Re. U.S. Appl. No. 12/792,856.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Official Action Dated Apr. 8, 2010 From the US Patent and Trademark Office Re.: U.S. Appl. No. 11/980,690.
Official Action Dated Dec. 8, 2009 From the US Patent and Trademark Office Re.: U.S. Appl. No. 11/132,320.
Official Action Dated Dec. 8, 2010 From the US Patent and Trademark Office Re. U.S. Appl. No. 11/980,690.
Official Action Dated Dec. 8, 2010 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Jan. 8, 2010 From the US Patent and Trademark Office Re.: U.S. Appl. No. 11/656,548.
Official Action Dated Apr. 9, 2010 From the US Patent and Trademark Office Re. U.S. Appl. No. 11/798,017.
Official Action Dated Apr. 9, 2010 From the US Patent and Trademark Office Re.: U.S. Appl. No. 11/798,017.
Official Action Dated Mar. 9, 2011 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Nov. 10, 2010 From the US Patent and Trademark Office Re. : U.S. Appl. No. 10/616,307.
Official Action Dated Nov. 10, 2010 From the US Patent and Trademark Office Re.: U.S. Appl. No. 10/836,223.

Official Action Dated Oct. 10, 2012 From the US Patent and Trademark Office Re. U.S. Appl. No. 11/798,017.
Official Action Dated Aug. 11, 2009 From the US Patent and Trademark Office Re. : U.S. Appl. No. 09/641,973.
Official Action Dated Jul. 11, 2011 From the US Patent and Trademark Office Re.: U.S. Appl. No. 11/980,683.
Official Action Dated Mar. 11, 2010 From the US Patent and Trademark Office Re.: U.S. Appl. No. 11/607,075.
Official Action Dated Oct. 11, 2012 From the US Patent and Trademark Office Re. U.S. Appl. No. 11/976,852.
Official Action Dated Jul. 12, 2007 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Official Action Dated Sep. 12, 2011 From the US Patent and Trademark Office Re. U.S. Appl. No. 12/087,150.
Official Action Dated Aug. 13, 2008 From the US Patent and Trademark Office Re. U.S. Appl. No. 11/769,826.
Official Action Dated Dec. 13, 2007 From the Its Patent and Trademark Office Re. : U.S. Appl. No. 10/616,301.
Official Action Dated May 13, 2009 From the US Patent and Trademark Office Re.: U.S. Appl. No. 11/798,017.
Official Action Dated Sep. 13, 2011 From the US Patent and Trademark Office Re. U.S. Appl. No. 11/976,852.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re. : U.S. Appl. No. 10/616,301.
Official Action Dated Dec. 15, 2011 From the US Patent and Trademark Office Re.: U.S. Appl. No. 10/343,792.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Jul. 15, 2009 From the US Patent and Trademark Office Re.: U.S. Appl. No. 10/616,301.
Official Action Dated Mar. 15, 2004 From the US Patent and Trademark Office Re. : U.S. Appl. No. 09/765,316.
Official Action Dated Mar. 15, 2011 From the US Patent and Trademark Office Re.: U.S. Appl. No. 10/343,792.
Official Action Dated Sep. 15, 2009 From the US Patent and Trademark Office Re. : U.S. Appl. No. 10/616,307.
Official Action Dated Sep. 15, 2009 From the US Patent and Trademark Office Re.: U.S. Appl. No. 10/836,223.
Official Action Dated Apr. 16, 2012 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Feb. 16, 2012 From the US Patent and Trademark Office Re. U.S. Appl. No. 11/747,378.
Official Action Dated Sep. 16, 2009 From the US Patent and Trademark Office Re.: U.S. Appl. No. 09/727,464.
Official Action Dated Jan. 17, 2006 From the United States Patent and Trademark Office Re.: U.S. Appl. No. 11/034,007.
Official Action Dated May 18, 2012 From the US Patent and Trademark Office Re. U.S. Appl. No. 11/989,223.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Dec. 19, 2012 From the US Patent and Trademark Office Re. U.S. Appl. No. 12/448,473.
Official Action Dated Jan. 19, 2012 From the US Patent and Trademark Office Re. U.S. Appl. No. 11/667,793.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Apr. 20, 2011 From the US Patent and Trademark Office Re. U.S. Appl. No. 11/798,017.
Official Action Dated Apr. 20, 2011 From the US Patent and Trademark Office Re.: U.S. Appl. No. 11/798,017.
Official Action Dated Dec. 20, 2011 From the US Patent and Trademark Office Re. U.S. Appl. No. 12/309,479.
Official Action Dated Jul. 20, 2009 From the US Patent and Trademark Office Re.: U.S. Appl. No. 11/980,617.
Official Action Dated Jun. 21, 2012 From the US Patent and Trademark Office Re. U.S. Appl. No. 12/309,479.
Official Action Dated Mar. 21, 2008 From the US Patent and Trademark Office Re.: U.S. Appl. No. 10/533,568.
Official Action Dated Sep. 21, 2009 From the US Patent and Trademark Office Re. U.S. Appl. No. 11/798,017.
Official Action Dated Sep. 21, 2009 From the US Patent and Trademark Office Re.: U.S. Appl. No. 11/798,017.
Official Action Dated Dec. 22, 2011 From the US Patent and Trademark Office Re. U.S. Appl. No. 12/514,785.
Official Action Dated Apr. 23, 2012 From the US Patent and Trademark Office Re. U.S. Appl. No. 11/932,987.
Official Action Dated Dec. 23, 2008 From the US Patent and Trademark Office Re.: U.S. Appl. No. 09/727,464.
Official Action Dated Feb. 23, 2010 From the US Patent and Trademark Office Re. : U.S. Appl. No. 09/641,973.
Official Action Dated Jan. 23, 2012 From the US Patent and Trademark Office Re. U.S. Appl. No. 12/087,150.
Official Action Dated Jun. 23, 2006 From the United States Patent and Trademark Office Re.: U.S. Appl. No. 09/727,464.
Official Action Dated May 23, 2011 From the US Patent and Trademark Office Re. U.S. Appl. No. 11/667,793.
Official Action Dated May 23, 2011 From the US Patent and Trademark Office Re. U.S. Appl. No. 11/980,690.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Official Action Dated Nov. 23, 2010 From the US Patent and Trademark Office Re.: U.S. Appl. No. 11/656,548.
Official Action Dated Jun. 25, 2008 From the US Patent and Trademark Office Re.: U.S. Appl. No. 10/616,301.
Official Action Dated Sep. 25, 2006 From the US Patent and Trademark Office Re. : U.S. Appl. No. 10/616,301.
Official Action Dated Nov. 26, 2008 From the US Patent and Trademark Office Re.: U.S. Appl. No. 10/240,239.
Official Action Dated Oct. 26, 2011 From the US Patent and Trademark Office Re.: U.S. Appl. No. 10/836,223.
Official Action Dated Apr. 27, 2011 From the US Patent and Trademark Office Re.: U.S. Appl. No. 10/836,223.
Official Action Dated Jul. 27, 2010 From the US Patent and Trademark Office Re.: U.S. Appl. No. 10/616,307.
Official Action Dated Oct. 27, 2011 From the US Patent and Trademark Office Re.: U.S. Appl. No. 11/656,548.
Official Action Dated Apr. 28, 2010 From the US Patent and Trademark Office Re.: U.S. Appl. No. 10/616,301.
Official Action Dated Aug. 28, 2009 From the US Patent and Trademark Office Re.: U.S. Appl. No. 10/240,239.
Official Action Dated Dec. 28, 2010 From the US Patent and Trademark Office Re.: U.S. Appl. No. 11/607,075.
Official Action Dated Dec. 28, 2012 From the US Patent and Trademark Office Re.: U.S. Appl. No. 10/343,792.
Official Action Dated Feb. 28, 2012 From the US Patent and Trademark Office Re.: U.S. Appl. No. 09/641,973.
Official Action Dated Jan. 28, 2011 From the US Patent and Trademark Office Re.: U.S. Appl. No. 09/641,973.
Official Action Dated Jun. 28, 2011 From the US Patent and Trademark Office Re. U.S. Appl. No. 11/628,074.
Official Action Dated Apr. 29, 2009 From the US Patent and Trademark Office Re.: U.S. Appl. No. 11/980,690.
Official Action Dated Jul. 30, 2012 From the US Patent and Trademark Office Re.: U.S. Appl. No. 11/980,683.

Official Action Dated Nov. 30, 2012 From the US Patent and Trademark Office Re. U.S. Appl. No. 12/514,785.
Official Action Dated Oct. 30, 2009 From the US Patent and Trademark Office Re.: U.S. Appl. No. 11/980,690.
Official Action Dated Sep. 30, 2008 From the US Patent and Trademark Office Re.: U.S. Appl. No. 10/616,301.
Official Action Dated Sep. 30, 2010 From the US Patent and Trademark Office Re. U.S. Appl No. 11/798,017.
Official Action Dated Sep. 30, 2010 From the US Patent and Trademark Office Re.: U.S. Appl. No. 11/798,017.
Official Action Dated Aug. 31, 2012 From the US Patent and Trademark Office Re. U.S. Appl. No. 11/980,653.
Official Action Dated Jan. 31, 2011 From the US Patent and Trademark Office Re. U.S. Appl. No. 11/667,793.
Restriction Official Action Dated Nov. 8, 2011 From the US Patent and Trademark Office Re. U.S. Appl. No. 12/309,479.
Restriction Official Action Dated Mar. 9, 2012 From the US Patent and Trademark Office Re. U.S. Appl. No. 11/976,852.
Restriction Official Action Dated Sep. 12, 2011 From the US Patent and Trademark Office Re. U.S. Appl. No. 11/980,653.
Restriction Official Action Dated Apr. 13, 2012 From the US Patent and Trademark Office Re. U.S. Appl. No. 11/989,223.
Restriction Official Action Dated Nov. 15, 2011 From the US Patent and Trademark Office Re. U.S. Appl. No. 11/980,683.
Restriction Official Action Dated Aug. 16, 2012 From the US Patent and Trademark Office Re. U.S. Appl. No. 12/448,473.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Summons to Attend Oral Proceedings Pursuant to Rule 115(1) EPC Dated Nov. 29, 2012 From the European Patent Office Re. Applicaion No. 06756259.5.
Supplemental Notice of Allowability Dated Oct. 24, 2011 From the US Patent and Trademark Office Re.: U.S. Appl. No. 11/607,075.
Supplemental Response After Interview Dated Aug. 4, 2010 to Official Action of Mar. 2, 2010 From the US Patent and Trademark Office Re.: U.S. Appl. No. 11/980,617.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report and the European Search Opinion Dated Nov. 13, 2012 From the European Patent Office Re. Application No. 06728347.3.
Supplementary European Search Report and the European Search Opinion Dated Mar. 16, 2011 From the European Patent Office Re. Application No. 05803689.8.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Supplementary Partial European Search Report Dated Sep. 4, 2007 From the European Patent Office Re.: Application No. 0 2716285.8.
Supplementary Partial European Search Report Dated Nov. 11, 2008 From the European Patent Office Re.: Application No. 01951883.6.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Nov. 1, 2007 from the International Searching Authority of the Patent Cooperation Treaty Re.: Application No. PCT/IL06/00840.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct. 10, 2006 From the International Searching Authority of the Patent Cooperation Treaty Re.: Application No. PCT/IL06/00059.
Written Opinion Dated Jul. 11, 2008 from the International Searching Authority of the Patent Cooperation Treaty Re.: Application No. PCT/IL06/01511.
Written Opinion Dated Oct. 15, 2008 From the International Searching Authority Re.: Application No. PCT/IL07/00918.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Berman et al. "Dual-Isotope Myocardial Perfusion SPECT With Rest Thallium-201 and Stress Tc-99m Sestamibi", Nuclear Cardiology, 12(2): 261-270, May 1994.
Bloch et al. "Application of Computerized Tomography to Radiation Therapy and Surgical Planning", Proceedings of the IEEE, 71(3): 351-355, Mar. 1983.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Bracco Diagnostics "Cardioteca®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Brown et al. "Method for Segmenting Chest CT Image Data Using an Anatomical Model: Preliminary Results", IEEE Transactions on Medical Imaging, 16(6): 828-839, Dec. 1997.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Charland et al. "The Use of Deconvolution and Total Least Squares in Recovering a Radiation Detector Line Spread Function", Medical Physics, 25(2): 152-160, Feb. 1998. Abstract Only!
Chengazi et al. "Imaging Prostate Cancer With Technetium-99m-7E11-C5.3 (CYT-351)", Journal of Nuclear Medicine, 38: 675-682, 1997.
Corstens et al. "Nuclear Medicine's Role in Infection and Inflammation", The Lancet, 354: 765-770, 1999.

Day et al. "Localization of Radioiodinated Rat Fibrogen in Transplanted Rat Tumors", Journal of the National Cancer Institute, 23(4): 799-812, 1959.
DeGrado et al. "Topics in Integrated Systems Physiology. Tracer Kinetic Modeling in Nuclear Cardiology", Journal of Nuclear Cardiology, 7: 686-700, 2000.
Del Guerra et al. "An Integrated PET-SPECT Small Animal Imager: Preliminary Results", Nuclear Science Symposium, IEEE Records, 1: 541-544, 1999.
Dewaraja et al. "Accurate Dosimetry in [131]I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Ellestad "Stress Testing: Principles and Practice", XP008143015, 5th Edition, p. 432, Jan. 1, 2003.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Gilland et al. "Simultaneous Reconstruction and Motion Estimation for Gated Cardiac ECT", IEEE Transactions on Nuclear Science, XP011077797, 49(5): 23442349, Oct. 1, 2002. p. 2344, Section 'Introduction', First §.
Gugnin et al "Radiocapsule for Recording the Ionizing Radiation in the Gastrointestinal Tract", UDC 615.417:616.34-005.1-073.916-71 (All-Union Scientific-Research Institute of medical Instrument Design, Moscow. Translated from Meditsinskaya Tekhnika, 1:21-25, Jan.-Feb. 1972).
Handrick et al. "Evaluation of Binning Strategies for Tissue Classification in Computed Tomography Images", Medical Imaging 2006: Image Processing, Proceedings of the SPIE, 6144: 1476-1486, 2006.
Hassan et al. "A Radiotelemetry Pill for the Measurement of Ionising Radiation Using a Mercuric Iodide Detector", Physics in Medicine and Biology, 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jan et al. "Preliminary Results From the AROPET", IEEE Nuclear Science Symposium Conference Record, Nov. 4-10, 2001, 3: 1607-1610, 2001.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.
Jessup "Tumor Markers—Prognostic and Therapeutic Implications for Colorectal Carcinoma", Surgical Oncology, 7: 139-151, 1998.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Kadrmas et al. "Static Versus Dynamic Teboroxime Myocardial Perfusion SPECT in Canines", IEEE Transactions on Nuclear Science, 47(3): 1112-1117, Jun. 2000.
Kinahan et al. "Attenuation Correction for a Combined 3D PET/CT Scanner", Medical Physics, 25(10): 2046-2053, Oct. 1998.
Kojima et al. "Quantitative Planar Imaging Method for Measurement of Renal Activity by Using a Conjugate-Emission Image and Transmission Data", Medical Physics, 27(3): 608-615, 2000. p. 608.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Lange et al. "EM Reconstruction Algorithms for Emission and Transmission Tomography", Journal of Computer Assisted Tomography, 8(2): 306-316, Apr. 1984.
Lavallee et al. "Building a Hybrid Patient's Model for Augmented Reality in Surgery: A Registration Problem", Computing in Biological Medicine, 25(2): 149-164, 1995.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Lin et al. "Improved Sensor Pills for Physiological Monitoring", NASA Technical Brief, JPL New Technology Report, NPO-20652, 25(2), 2000.
Links "Advances in SPECT and PET Imaging", Annals in Nuclear Medical Science, 13(2): 107-120, Jun. 2000.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Iridium In-111 Pentetreotide. Diagnostic—for Intravenous Use. Rx Only", Mallinckrodt Inc., Product Sheet, 2 P., Oct. 25, 2006.
Mao et al. "Human Prostatic Carcinoma: An Electron Microscope Study", Cancer Research, XP002625777, 26(5): 955-973, May 1966.
McJilton et al. "Protein Kinase C? Interacts With Bax and Promotes Survival of Human Prostate Cancer Cells", Oncogene, 22; 7958-7968, 2003.
Mettler et al. "Legal Requirements and Radiation Safety", Essentials of Nuclear Medicine Imaging, 2nd Ed., Chap.13: 323-331, 1985.
Meyers et al. "Age, Perfusion Test Results and Dipyridamole Reaction", Radiologic Technology, XP008142909, 73(5): 409-414, May 1, 2002.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Mori et al. "Overexpression of Matrix Metalloproteinase-7mRNA in Human Colon Carcinomas", Cancer, 75: 1516-1519, 1995.
Ogawa et al. "Ultra High Resoultion Pinhole SPECT", IEEE Nuclear Science Symposium, 2: 1600-1604, 1998.
Ohno et al. "Selection of Optimum Projection Angles in Three Dimensional Myocardial SPECT", IEEE Nuclear Science Symposium Conference Record 2001, 4: 2166-2169, 2001.
Ohrvall et al. "Intraoperative Gamma Detection Reveals Abdominal Endocrme Tumors More Efficiently Than Somatostatin Receptor Scintigraphy", 6th Conference on Radioimmunodetection and Radioimmunotherapy of Cancer, Cancer, 80: 2490-2494, 1997.
Ouyang et al. "Incorporation of Correlated Structural Images in PET Image Reconstruction", IEEE Transactions of Medical Imaging, 13(4): 627-640, Dec. 1994.

Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.

Pellegrini et al. "Design of Compact Pinhole SPECT System Based on Flat Panel PMT", IEEE Nuclear Science Symposium Conference Record, 3: 1828-1832, 2003.

Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.

Piperno et al. "Breast Cancer Screening by Impedance Measurements", Frontiers Med. Biol. Engng., 2(2): 11-17, 1990.

Pluim et al. "Image Registration by Maximization of Combined Mutual Information and Gradient Information", IEEE Transactions on Medical Imaging, 19(8): 1-6, 2000.

Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.

Quartuccia et al. "Computer Assisted Collimation Gama Camera: A New Approach to Imaging Contaminated Tissues", Radiation Projection Dosimetry, 89(3-4): 343-348, 2000.

Rajshekhar "Continuous Impedence Monitoring During CT-Guided Stereotactic Surgery: Relative Value in Cystic and Solid Lesions", British Journal of Neurosurgery, 6: 439-444, 1992.

Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.

Reutter et al. "Kinetic Parameter Estimation From Attenuated SPECT Projection Measurements", Wee Transactions on Nuclear Science, 45(6): 3007-3013, 1998.

Rockmore et al. "A Maximum Likelihood Approach to Emission Image Reconstruction From Projections", IEEE Transactions on Nuclear Science, 23(4): 1428-1432, Aug. 1976.

Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.

Sands et al. "Methods for the Study of the Metabolism of Radiolabeled Monoclonal Antibodies by Liver and Tumor", The Journal of Nuclear Medicine, 28: 390-398, 1987.

Seret et al. "Intrinsic Uniformity Requirements for Pinhole SPECT", Journal of Nuclear Medicine Technology, 34(1): 43-47, Mar. 2006.

Shepp et al. "Maximum Likelihood Reconstruction for Emission Tomography", IEEE Transactions on Medical Imaging, MI-1: 113-122, Oct. 1982.

Sitek et al. "Reconstruction of Dynamic Renal Tomographic Data Acquired by Slow Rotation", The Journal of Nuclear Medicine, 42(11): 1704-1712, Nov. 2001.

Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.

Solanki "The Use of Automation in Radiopharmacy", Hospital Pharmacist, 7(4): 94-98, Apr. 2000.

Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2—p. 585, § 1.

Storey et al. "Tc-99m Sestamibi Uptake in Metastatic Prostate Carcinoma", Clinical Nuclear Medicine, XP009145398, 25(2): 133-134, Feb. 2000.

Takahashi et at "Attenuation Correction of Myocardial SPECT Images With X-Ray CT: Effects of Registration Errors Between X-Ray CT and SPECT", Annals of Nuclear Medicine, 16(6): 431-435, Sep. 2002.

Thorndyke et al. "Reducing Respiratory Motion Artifacts in Positron Emission Tomography Through Retrospective Stacking", Medical Physics, 33(7): 2632-2641, Jul. 2006.

Toennies et al. "Scatter Segmentation in Dynamic SPECT Images Using Principal Component Analysis", Progress in Biomedical Optics and Imaging, 4(23): 507-516, 2003.

Tomai et al. "A 3D Gantry Single Photon Emission Tomograph With Hemispherical Coverage for Dedicated Breast Imaging", Nuclear Instruments & Methods in Physics Research, Section A, 497: 157-167, 2003.

Trikha et al. "Monoclonal Antibodies as Therapeutics in Oncology", Current Opinion in Biotechnology, 13: 609-614, 2002.

Volkow et al. "Imaging the Living Human Brain: Magnetic Resonance Imaging and Positron Emission Tomography", Proc. Natl. Acad. Sci. USA, 94: 2787-2788, Apr. 1997.

Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.

Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.

Wu et al. "ECG-Gated Pinhole SPECT in Mice With Millimeter Spatial Resolution", IEEE Transactions on Nuclear Science, 47(3): 1218-1221, Jun. 2000.

Xu et al. "Quantitative Expression Profile of Androgen-Regulated Genes in Prostate Cancer Cells and Identification of Prostate-Specific Genes", International Journal of Cancer, 92: 322-328, 2001.

Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.

Zaidi et al. "Magenetic Resonance Imaging-Guided Attenuation and Scatter Corrections in Three-Dimensional Brain Positron Emission Tomography", Medical Physics, 30(5): 937-948, May 2003.

Zaidi et al. "MRI-Guided Attenuation Correction in 3D Brain PET", Neuroimage Human Brain Mapping 2002 Meeting, 16(2): Abstract 504, Jun. 2002.

Zhang et al. "An Innovative High Efficiency and High Resolution Probe for Prostate Imaging", The Journal of Nuclear Medicine, 68: 18, 2000. Abstract.

Zhang et al. "Potential of a Compton Camera for High Performance Scintimammography", Physics in Medicine and Biology, XP020024019, 49(4): 617-638, Feb. 21, 2004.

Advisory Action Before the Filing of an Appeal Brief Dated Feb. 26, 2013 From the US Patent and Trademark Office Re. U.S. Appl. No. 12/514,785.

Notice of Allowance Dated Feb. 21, 2013 From the US Patent and Trademark Office Re. U.S. Appl. No. 11/798,017.

Notice of Allowance Dated Feb. 25, 2013 From the US Patent and Trademark Office Re.: U.S. Appl. No. 09/641,973.

Notice of Allowance Dated Feb. 27, 2013 From the US Patent and Trademark Office Re. U.S. Appl. No. 12/514,785.

Advisory Action Before the Filing of an Appeal Brief Dated Feb. 26, 2013 From the US Patent and Trademark Office Re. U.S. Appl. No. 11/989,223.

Advisory Action before the Filing of an Appeal Brief Dated May 21, 2013 From the US Patent and Trademark Office Re. U.S. Appl. No. 11/980,653.

Applicant-Initiated Interview Summary Dated May 1, 2013 From the US Patent and Trademark Office Re. U.S. Appl. No. 10/343,792.

Applicant-Initiated Interview Summary Dated May 1, 2013 From the US Patent and Trademark Office Re. U.S. Appl. No. 11/980,653.

Applicant-Initiated Interview Summary Dated May 9, 2013 From the US Patent and Trademark Office Re. U.S. Appl. No. 12/448,473.

Official Action Dated Mar. 11, 2013 From the US Patent and Trademark Office Re. U.S. Appl. No. 13/345,719.

Official Action Dated Nov. 30, 2012 From the US Patent and Trademark Office Re. U.S. Appl. No. 11/989,223.

* cited by examiner

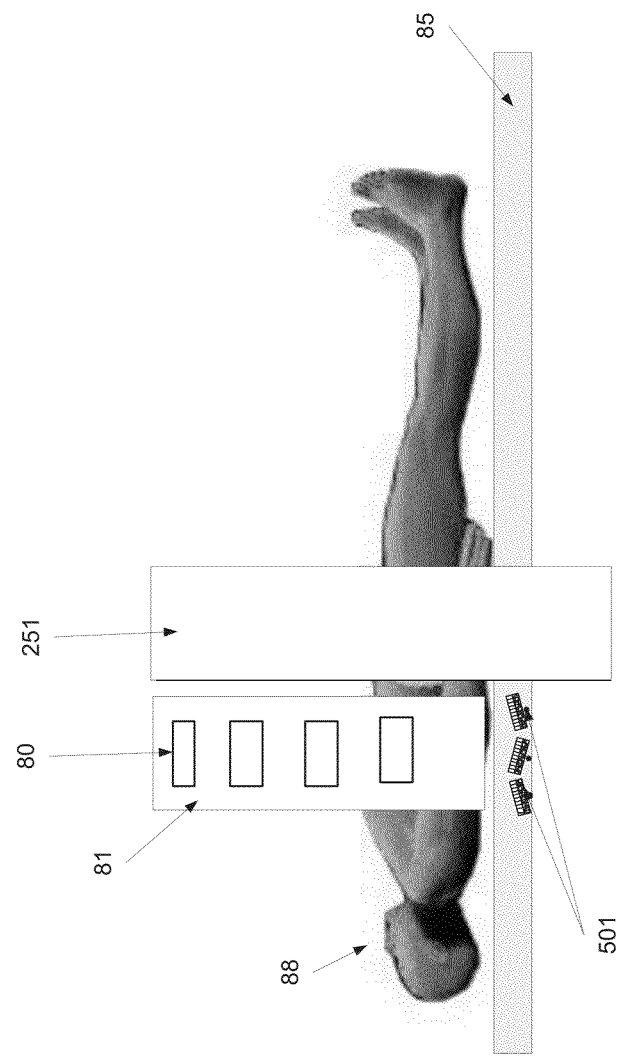

METHOD AND SYSTEM OF OPTIMIZED VOLUMETRIC IMAGING

RELATED APPLICATIONS

This application is a continuation of U.S. patent application Ser. No. 12/792,856 filed on Jun. 3, 2010, which claims the benefit of priority under 35 USC 119(e) from U.S. Provisional Patent Application No. 61/229,549 filed on Jul. 29, 2009.

This application incorporates by reference U.S. Provisional Patent Application No. 61/229,549 filed on Jul. 29, 2009, International Patent Application No. PCT/IL2005/001173 filed on Nov. 9, 2005 (PCT Publication No. WO2006/051531 published May 18, 2006) and International Patent Application No. PCT/IL2006/000834 filed on Jul. 19, 2006 (PCT Publication No. WO2007/010534 published Jan. 25, 2007).

The contents of the above applications are incorporated herein by reference in their entirety.

FIELD AND BACKGROUND OF THE INVENTION

The present invention, in some embodiments thereof, relates to method and system of imaging and, more particularly, but not exclusively, to method and system of medical imaging.

Volumetric scans such as CAT scans, PET scans, CT scans, MRI scans, Ultrasound scans, Laser 3D scanners, and the like are commonly used, particularly in the medical industry, to observe objects within a structure that would otherwise be unobservable. These scans have greatly advanced the capability of professionals such as doctors. Conventional volumetric scan is intended to produce a volumetric image of a large volume of the body at high resolution. The ability to perform a volumetric scan with high resolution requires a large number of detectors, a fine motion control, and abundant processing resources for allowing the acquisition of a high resolution volumetric image in a reasonable time. Furthermore, as the volumetric scan images a relatively large area, such as the torso, the patient radiation dose is relatively high, for example when the volumetric scan is a CT scan.

Usually, volumetric imaging of a body structure is a multi-stage process. First biochemical, radioactive and/or contrast agents may be administered. Then, measurements are taken at a set of predetermined views at predetermined locations, orientations, and durations. Then, the data is analyzed to reconstruct a volumetric image of the body structure and an image of the body structure is formed. The imaging process is sequential, and there is no assessment of the quality of the reconstructed image until after the measurement process is completed. Where a poor quality image is obtained, the measurements must be repeated, resulting in inconvenience to the patient and inefficiency in the imaging process.

The volumetric scan is usually performed by orbiting detectors from multiple directions in order to provide sufficient information to reconstruct a three-dimensional image of the radiation source by means of computed tomography. The detectors are typically mounted on a gantry to provide structural support and to orbit the detector around the object of interest. If the detector is a nuclear medicine detector, such as scintillation detector or CZT detectors, for example Single photon emission computed tomography single photon emission computed tomography (SPECT) and positron emission tomography (PET) systems detector, a collimator that is used to restrict radiation acceptance, or the direction of ray travel, is placed between it and the object being imaged. Typically this collimator is constructed to provide a multiplicity of small holes in a dense, high-atomic-number material such as lead or Tungsten. The rays will pass through the holes if they travel in a direction aligned with the hole but will tend to be absorbed by the collimator material if they travel in a direction not aligned with the holes.

During the last years, a number of non-orbiting tomographic imaging systems have been developed. For example U.S. Pat. No. 6,242,743, filed on Aug. 11, 1998 describes tomographic imaging system which images ionizing radiation such as gamma rays or x rays and which: 1) can produce tomographic images without requiring an orbiting motion of the detector(s) or collimator(s) around the object of interest, 2) produces smaller tomographic systems with enhanced system mobility, and 3) is capable of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with collimators in a combination of application-specific acquisition geometries and non-orbital detector module motion sequences composed of tilting, swiveling and translating motions, and combinations of such motions. Various kinds of module geometry and module or collimator motion sequences are possible, and several combinations of such geometry and motion are shown. The geometric configurations may be fixed or variable during the acquisition or between acquisition intervals. Clinical applications of various embodiments of the tomography invention include imaging of the human heart, breast, brain or limbs, or small animals. Methods of using the non-orbiting tomographic imaging system are also included.

Another example is described in United States Patent Application 2010/0001200, published on Jul. 1, 2010, which describes an imaging system for radioimaging a region of interest (ROI) of a subject. The system includes a housing, a support structure, which is movably coupled to the housing, and at least one motor assembly, coupled to the housing and the support structure, and configured to move the support structure with respect to the housing. The system also includes at least two detector assemblies, fixed to the support structure, and comprising respective radiation detectors and angular orientators. A control unit drives the motor assembly to position the support structure in a plurality of positions with respect to the housing, and, while the support structure is positioned in each of the plurality of positions, drives the orientators to orient the respective detectors in a plurality of rotational orientations with respect to the ROI, and to detect radiation from the ROI at the rotational orientations. Other embodiments are also described.

SUMMARY OF THE INVENTION

According to some embodiments of the present invention there is provided a system of performing a volumetric scan. The system comprises a surface of positioning a patient in a space parallel thereto, a plurality of extendable detector arms each the detector arm having a detection unit having at least one radiation detector, and an actuator which moves the detection unit along a linear path, and a gantry which supports the plurality of extendable detector arms around the surface so that each the linear path of each respective the extendable detector arm being directed toward the space.

Optionally, the system further comprises a controller for controlling each the actuator to move a respective the detection unit along the linear path according to a scanning pattern.

Optionally, the detection unit comprises a tilting mechanism for tilting the at least one radiation detector in a sweeping motion.

Optionally, the gantry is configured for radially disposing the plurality of extendable detector arms along an arch above the surface.

Optionally, the at least one radiation detector comprises at least one nuclear medicine (NM) detector.

Optionally, each the extendable detector arm comprises an X-ray radiation source and the at least one radiation detector being set to intercept a reflection of X-ray radiation emitted from the X-ray radiation source.

More optionally, the X-ray radiation source is part of the detection unit.

More optionally, the at least one radiation detector intercepts both the reflection and Gamma ray radiation emitted from the body of the patient.

More optionally, each the detection unit operates both in a photon counting mode and in a flux measurement mode.

Optionally, the gantry rotates the plurality of extendable detector arms around the body of the patient.

Optionally, the surface is at least one of a horizontal surface or a vertical surface embedded with a plurality of additional radiation detectors.

Optionally, the surface is at least one of a bed, a chair and a wall.

More optionally, at least one of the plurality of detection units comprises a proximity detector which estimates a distance between a tip of a respective the extendable detector arm and the body of the patient, the controller controls each respective the actuator according to respective the distance.

More optionally, at least one of the plurality of detection units comprises a pressure detector which estimates a pressure applied on the body of the patient by a tip of a respective the extendable detector arm, the controller controls each respective the actuator according to respective the pressure.

Optionally, at least one of the plurality of detection units comprises an attenuation correction detector which captures additional radiation emitted from the body of the patient to correct a reconstruction of a volumetric image by radiation intercepted by respective the at least one radiation detector.

More optionally, the attenuation correction detector is an ultrasonic (US) to transducer.

More optionally, the system further comprises a breathing detector which monitors thoracic movements of the patient; the controller controls at least one of the plurality of actuators according to the monitoring.

Optionally, the linear path extends from a plane defined by the gantry.

Optionally, the linear path is diagonal to the surface.

More optionally, the actuator rotates each the detection unit around an axis parallel to a respective the linear path.

Optionally, the system further comprises at least one additional gantry each supports a plurality of extendable detector arms around the surface in a similar manner to the manner the gantry supports the plurality of extendable detector arms.

More optionally, the tips of the plurality of extendable detector arms and the plurality of extendable detector arms are extended toward a common axial plane of the body of the patient.

Optionally, the system further comprises at least one tilting motor which tilts at least one of the plurality of extendable detector arms in relation to the gantry.

Optionally, each the detection unit comprises an array of a plurality of radiation detectors, each set to move in sweeping motion.

According to some embodiments of the present invention there is provided a method of performing a volumetric scan that comprises a) providing a surface of positioning a patient in a space parallel thereto, b) linearly moving a plurality of detection units, each having at least one radiation detector, from a plurality of distinct locations along a framework around the surface toward a plurality of points each at a less than a predefined distance from the body of the patient, c) intercepting radiation from the patient using each the at least one radiation detector, and d) reconstructing a volumetric image of at least one part of the patient's body according to the radiation.

Optionally, the method further comprises radially disposing plurality of detection units to a plurality of new locations and repeating the c) and d) from the plurality of new locations.

Optionally, the plurality of points comprises a plurality of points of contact with the body of the patient.

Optionally, the plurality of points comprises a plurality of points of proximity from the body, each the point of proximity being at a distance of less than 5 cm from the body.

Optionally, the distinct locations are at least 5 cm from one another.

Optionally, the intercepting comprises tilting each the at least one radiation detector in sweeping motion at the point of contact.

Optionally, the method further comprises selecting a group of the plurality of detection units according to a dimension of the body of the patient, the linearly moving comprising linearly moving only members the group.

Optionally, the linearly moving comprises, for each the detection unit, detecting a distance from the body of the patient and linearly moving respective the radiation detector according to the distance.

Optionally, the linearly moving comprises, using an actuator to move the detection unit toward the body of the patient until a pressure applied by the actuator is above a threshold.

Optionally, the linearly moving comprises monitoring breathing of the patient and controlling the linear motion according to the monitoring.

Optionally, the system further comprises changing at least one of emission and orientation of the plurality of detection units so as to increase the resolution of the volumetric image in at least one region of interest in relation to other regions of the volumetric image and repeating the b)-d).

According to some embodiments of the present invention there is provided a system of performing a volumetric scan. The system comprises a surface of positioning a patient in a space parallel thereto, a plurality of radiation detectors embedded in the surface and set to intercept radiation emitted from of at least one part of the patient's body, and a reconstruction module which reconstructs a volumetric image of the at least one part according to the intercepted radiation.

Optionally, the system further comprises of actuating unit for actuating the plurality of radiation detectors according to a scanning pattern.

Optionally, the system further comprises a gantry which supports a plurality of additional radiation detectors above the surface, the additional radiation detectors are set to intercept additional radiation emitted from of the at least one part, the reconstruction module reconstructs the volumetric image according to a combination of the intercepted radiation and the intercepted additional radiation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6A is a schematic illustration of an arrangement having a CT scanner and the volumetric scanner, according to some embodiments of the present invention;

DESCRIPTION OF EMBODIMENTS OF THE INVENTION

The present invention, in some embodiments thereof, relates to method and system of imaging and, more particularly, but not exclusively, to method and system of medical imaging.

According to some embodiments of the present invention there is provided a system of performing a volumetric scan of at least a part of a body of a patient, such as a volumetric scanner, using a plurality of radiation detectors which are moved toward the body of the patient, and are capable of local translation or rotation, optionally separately.

The system includes a patient surface of positioning the patient in a space parallel thereto. The patient surface may be adjusted to support standing patients, laying patients, seating patients, and/or leaning patients. For example, the surface may be a horizontal alignment surface, such as a patient bed, a vertical alignment surface, such as a wall or a back of a chair and the like.

Figure 7:
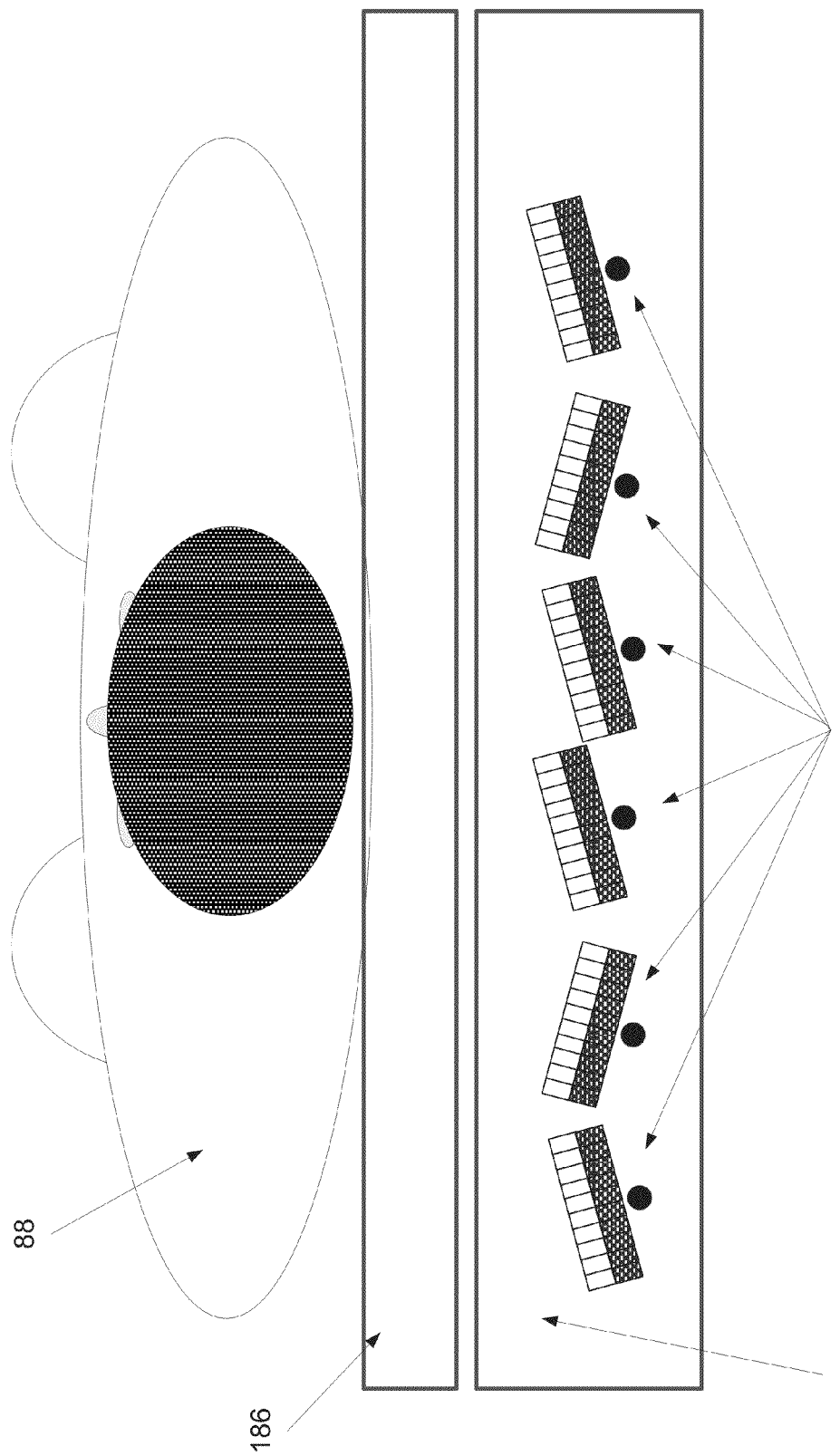
FIG. 7 is a sectional schematic illustration of an exemplary back surface, along its latitudinal axis, below a pad on which a patient lies, according to some embodiments of the present invention.

The patient surface is optionally embedded with a plurality of radiation detectors intercepts radiation emitted or reflected from the patient, for example as shown at FIG. 7. In other embodiments, the radiation detectors are placed in the patient surface that is placed below or in a pad on which a patient lies.

For brevity radiation emitted, transmitted through or reflected from the patient may be referred to herein as radiation emitted from the patient. The system further includes a plurality of extendable detector arms. Each extendable detector arm has a detection unit with one or more radiation detectors, such as nuclear medicine detectors, and an actuator that moves the detection unit along a linear path toward and from the body of the patient. The system further includes a gantry, optionally annular or semiannular, which supports the arms around the patient. In use, the patient may horizontally positioned on the surface, and the extendable detector arms may be used for bringing the detection units to points in a predefined distance from the body of the patient and/or to points of contact with the body of the patient. The projection of radiation, such as gamma radiation, which is intercepted by the detectors of the detection units allow reconstructing a volumetric image. Optionally, each detection unit includes a radiation source, such as an X-ray source that allows transmitting radiation into the body of the patient. In such embodiments, a volumetric image may be reconstructed according to both gamma and x-ray radiation which is emitted and reflected from the body of the patient. Optionally, the extendable detector arms and/or the gantry may be rotated tilted, and/or moved along the patient surface according to a scanning pattern and/or user instructions.

Optionally, the number of extendable detector arms which are used for reconstructing the volumetric image dependents on the dimension of the patient. In such an embodiment, a limited number of extendable detector arms may be used for imaging a thin patient and a larger number of extendable detector arms may be used for imaging an obese patient. Optionally, a number of gantries with extendable detector arms are used for reconstructing a volumetric image of a patient. In such an embodiment, a single gantry may be used for imaging a thin patient and a number of gantries may be used for imaging an obese patient.

According to some embodiments of the present invention, there is provided a system of performing a volumetric scan. The system includes a surface of positioning a patient in a space parallel thereto, such as a bed, and a plurality of radiation detectors which may be embedded into the surface, which may be placed below a pad on which the patient lies, and set to intercept radiation emitted from of at least one part of the patient's body, for example and as outlined above and described below. The system further includes a reconstruction module that reconstructs a volumetric image of the at least one part according to the intercepted radiation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
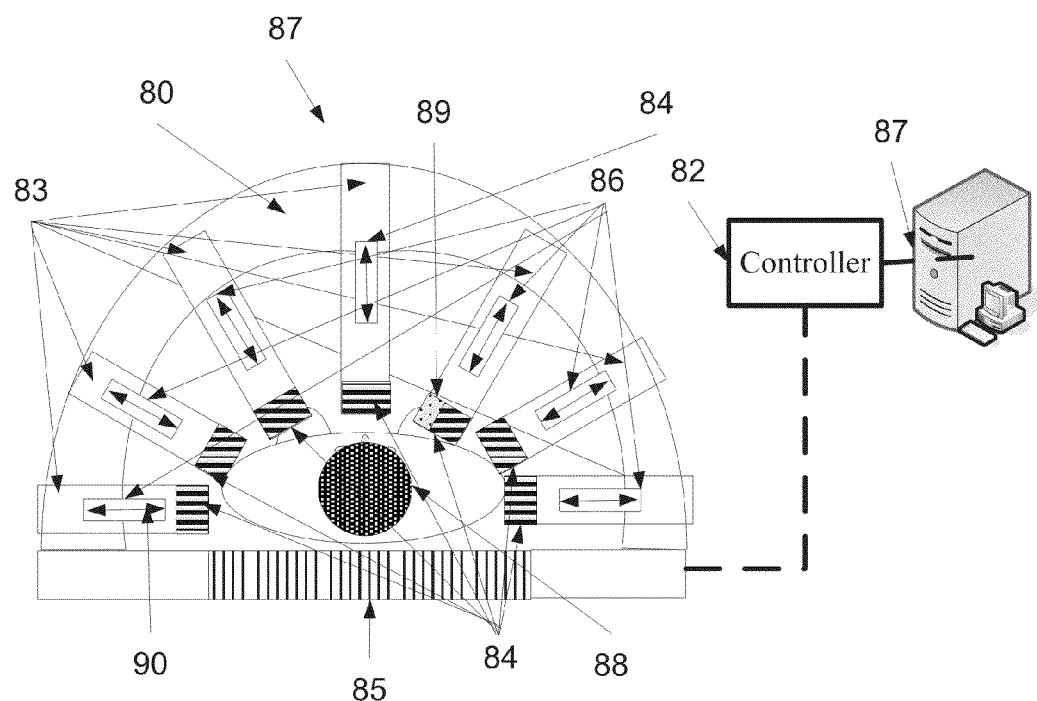
FIG. 1 is a sectional schematic illustration of a volumetric scanner having a gantry radially supporting a plurality of extendable detector arms, according to some embodiments of the present invention.

Reference is now made to FIG. 1, which is a sectional schematic illustration of a system, such as a volumetric scanner 81, for example a nuclear medicine (NM) scanner, having a gantry 80 radially supporting a plurality of extendable detector arms 83, optionally having their tips directed toward a common volumetric area above patient's bed 805, according to some embodiments of the present invention. Optionally, the volumetric scanner 81 allows capturing a Clinically-Valuable Image of the patient, as defined below.

As used herein, an extendable detector arm means having a detector arm having a varying length. The gantry 80 is optionally an annular and/or semiannular frame that is designed to be placed around a surface 85 of positioning a patient for scanning in a space, such as a bed, referred to herein as a patient surface, for example as shown in FIG. 1. Each extendable detector arm 83 may include a linear actuator 86 and a detection unit 84 that is connected to its tip for intercepting radiation from the scanned patient. For brevity, the term patient may be used to describe any body portion of a patient, for example one or more organs and/or a portion of an organ. The detection unit 84 includes one or more radiation detectors, such as semiconductor radiation detectors, for example nuclear medicine (NM) detectors, for instance cadmium zinc telluride (CZT) detectors. The linear actuator 86 is designed to linearly maneuver the detection unit 84 toward and from a location in a space bounded or otherwise defined by gantry 80. Optionally, the linear actuator 86 is mechanical actuator that converts rotary motion of a control knob into linear displacement, a hydraulic actuator or hydraulic cylinder, for example a hollow cylinder having a piston, a piezoelectric actuator having a voltage dependent expandable unit, and/or an electro-mechanical actuator that is based on an electric motor, such a step motor and the like. The linear actuators 86 of the extendable detector arms 83 are connected to a controller 82 which converts digital signals of a scanning computing unit 82 into electronic signals necessary to control it. The control of each linear detector actuator 83 is performed according to a volumetric scanning pattern calculated and/or controlled by the scanning computing unit 82 and/or attenuation correction/scatter corrections (ACSCs), for example corrections of breathing motions, optionally calculated according to feedback from one or more sensors, such as position sensors, which sense the actual location of the tip of the respective extendable detector arm 83. As the extendable detector arms includes only some of the total detection units 84 which are used in the volumetric scanner 81, motion control which require about 1 Kg moving force or less may be enabled. As such, they do not apply extensive force on the patient and may easily get in contact with the patient's skin by using linear actuator 86, such as a pneumatic actuator.

When a patient 88 is positioned horizontally on the patient surface 85, the controller 82 instructs the linear actuators 86 to extend toward the patient's body in a space above the patient surface 85, for example along the linear axes depicted in FIG. 1, such as numeral 90. Optionally, the instructions are provided according to a volumetric scanning pattern calculated and/or controlled by a scanning computing unit 87. Optionally, contrast materials, contrast agents and/or contrast mediums, are injected to the patient 88 before the scanning process. The contrast material may include any internally administered substance that has, when imaged by the CT scanner, a different opacity from soft tissue on computed tomography, for example Barium, water, Iodine, and/or Sterile saline.

Optionally, some or all of the extendable detector arms 83 have a proximity detector, for example as shown at 89, such as an electrostatic touch sensor, a capacitive, an infrared (IR) detector or an acoustic proximity detector, such as an ultrasonic (US) transducer. The proximity detector 89 is electrically connected to the controller 82 so as to allow the controller 82 to receive its feedback. The proximity detector 89 indicates when the tip of the extendable detector arms 83 and/or the detection unit 84 is in a certain distance from the body of the patient 88. Optionally, the controller instructs the extending of the extendable detector arms 83 until the proximity detector 89 feedback indicates that the tip of the extendable detector arms 83 is in touch with the body of the patient 88. Optionally, any group of extendable detector arms 83 may be extended together, for example a group of 1, 2, 3, 4, 5, 6, 7, and 8 extendable detector arms 83. Optionally, the proximity detector 89 includes a pressure sensor which indicates when the tip of the extendable detector arm 83 applies a certain amount of pressure on the body of the patient. In such a manner, the proximity detector 89 can indicate that the tip of the extendable detector arm 83 is held firmly against the body of the patient. Optionally, the pressure applied by each extendable detector arm 83 is no more than 1 kilogram (Kg). Optionally, the proximity detector 89 is placed about 1 centimeter (cm) from the tip of the extendable detector arm 83.

Optionally, some or all of the extendable detector arms 83 have a breathing detector, such as an US transducer which monitors the breathing of the patient 88 for example by monitoring her thoracic movements. In such an embodiment, the extending of the extendable detector arms 83 may be coordinated with the breathing cycle of the patient. Optionally, the same detector is used as a proximity detector and as a breathing detector, for example a US transducer. Optionally, the same detector is also used as a pressure detector.

Figure 2A:
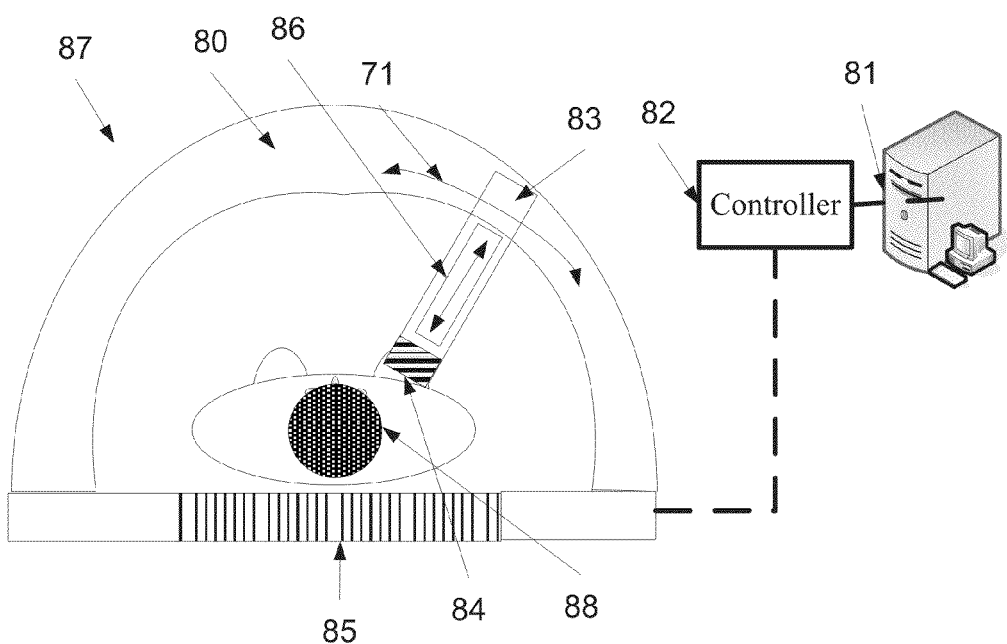
FIG. 2A is a sectional schematic illustration of the volumetric scanner where a disposition of one of the extendable detector arms along an arch is depicted, according to some embodiments of the present invention.

Optionally, as shown at FIG. 2A, each one of the extendable detector arms 83 may be radially disposed 71 along an arch or a perimeter of a circle centered at a location above the patient surface 85. Optionally, any group of extendable detector arms 83 may be radially disposed 71 together. The movement of the extendable detector arm 83 is optionally defined by a path, such as a groove, in the gantry 80 and controlled by the controller 82, for example according to a volumetric scanning pattern calculated and/or controlled by the scanning computing unit 82. Optionally, one or more motors actuate the movement of each extendable detector arm 83 along the arch or perimeter according to the outputs of the controller 82.

Optionally, the gantry 80 may be rotated tilted, and/or moved along the patient surface 85 according to the outputs of the controller 82 and/or user instructions.

Figure 6B:
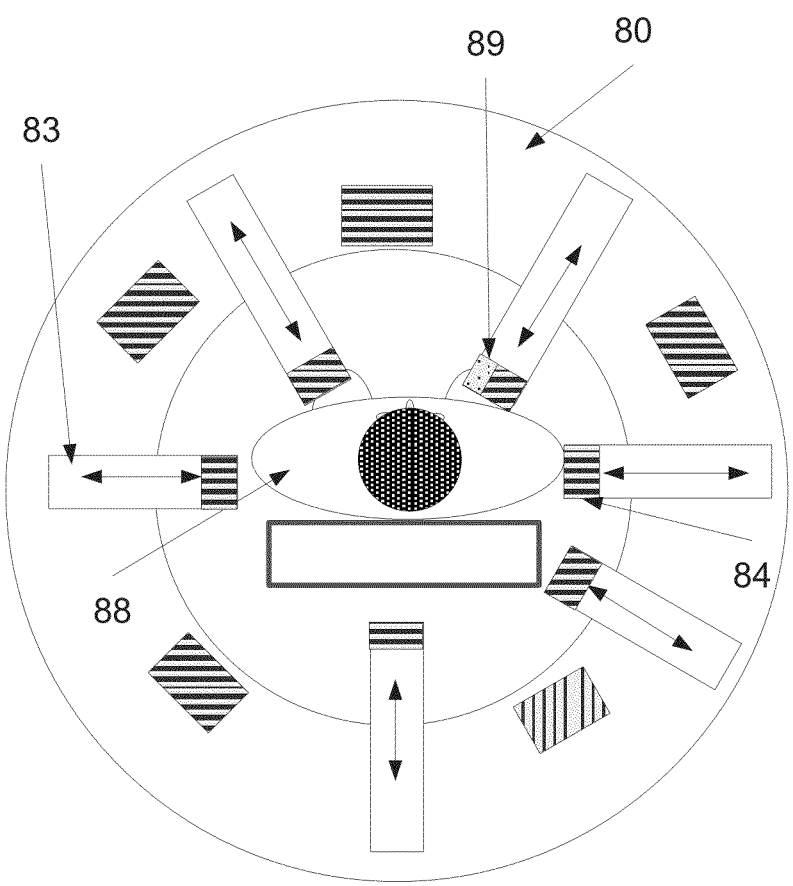
FIG. 6B a sectional schematic illustration of a circular gantry, according to some embodiments of the present invention.

According to some embodiments of the present invention, the gantry 80 is circular, for example as shown at FIG. 6B. Optionally, the volumetric scanner 81 allows capturing a Clinically-Valuable Image of the patient, as defined below. In such an embodiment, the gantry may be used to rotate the extendable detector arms 83 around the patient 88. Optionally, the extendable detector arms 83 are rotated while being in contact with the body of the patient 88 and/or in proximity to the body of the patient 88.

Figure 2B:
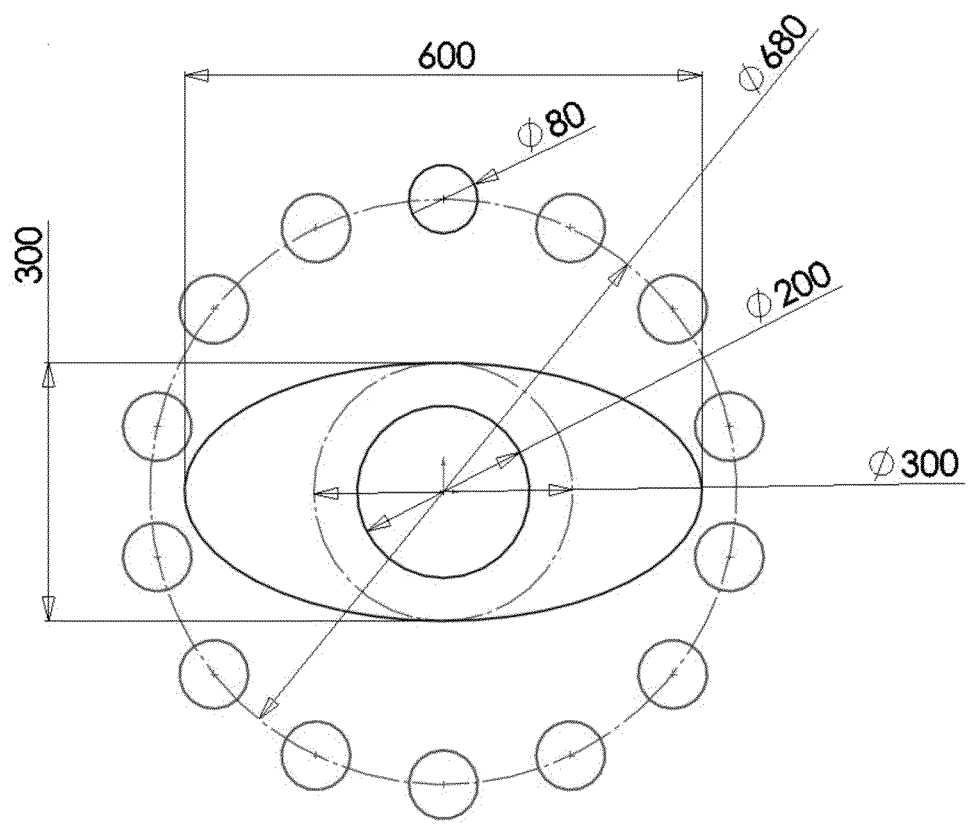
FIGS. 2B-2D are sectional schematic illustrations of a plurality of detection units mounted on a circular gantry which may change the proximity of detection units from the body of a patient, according to some embodiments of the present invention.
Figure 2D:
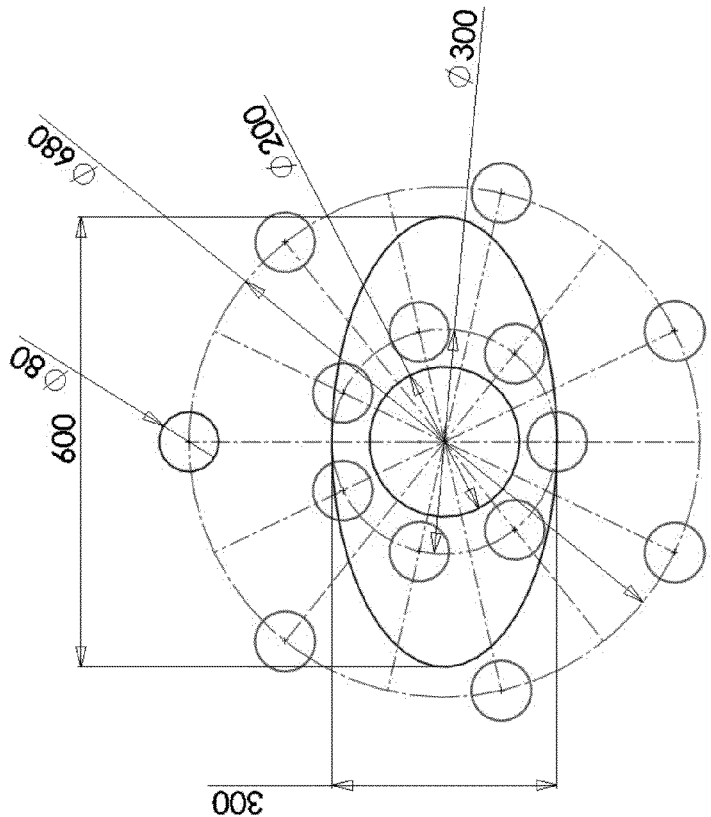
Figure 2C:
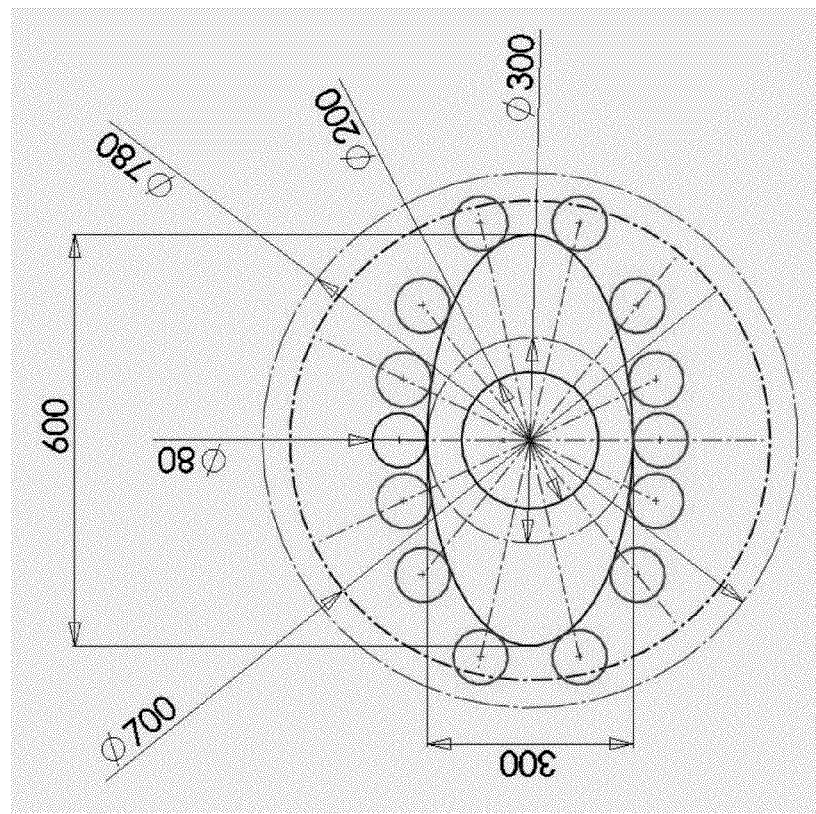

Reference is now made to FIGS. 2B-2D, which are sectional schematic illustrations of a circular gantry 80 having a plurality of detection units 84, according to some embodiments of the present invention. Though the detection units 84 are depicted as circular elements, they may have various forms and may be actuated as described above in relation to FIGS. 1 and 2. In FIG. 2B, the detection units 84 are located away from the body of the patient 88. FIG. 2C depicts the detection units 84 when they are located in a plurality of contact points with the body of the patient 88 or in a plurality of proximity points from the body of the patient 88.

In FIG. 2D, only some of the detection units 84 are located in a plurality of contact points with the head of the patient 88 or in a plurality of proximity points from the head of the patient 88. As further described below, group of detection units 84 may be used to image thin patients and/or organs with limited perimeters while others are idle. In such a manner, the number of detection units 84 which are used in each scan is dynamic, allowing using the same scanner for scanning various organs and/or patients from a plurality of contact and/or proximity points with and/or from the patient 88. FIGS. 2B-2D further depict exemplary perimeters and radiuses of the volumetric scanner 81.

Figure 3:
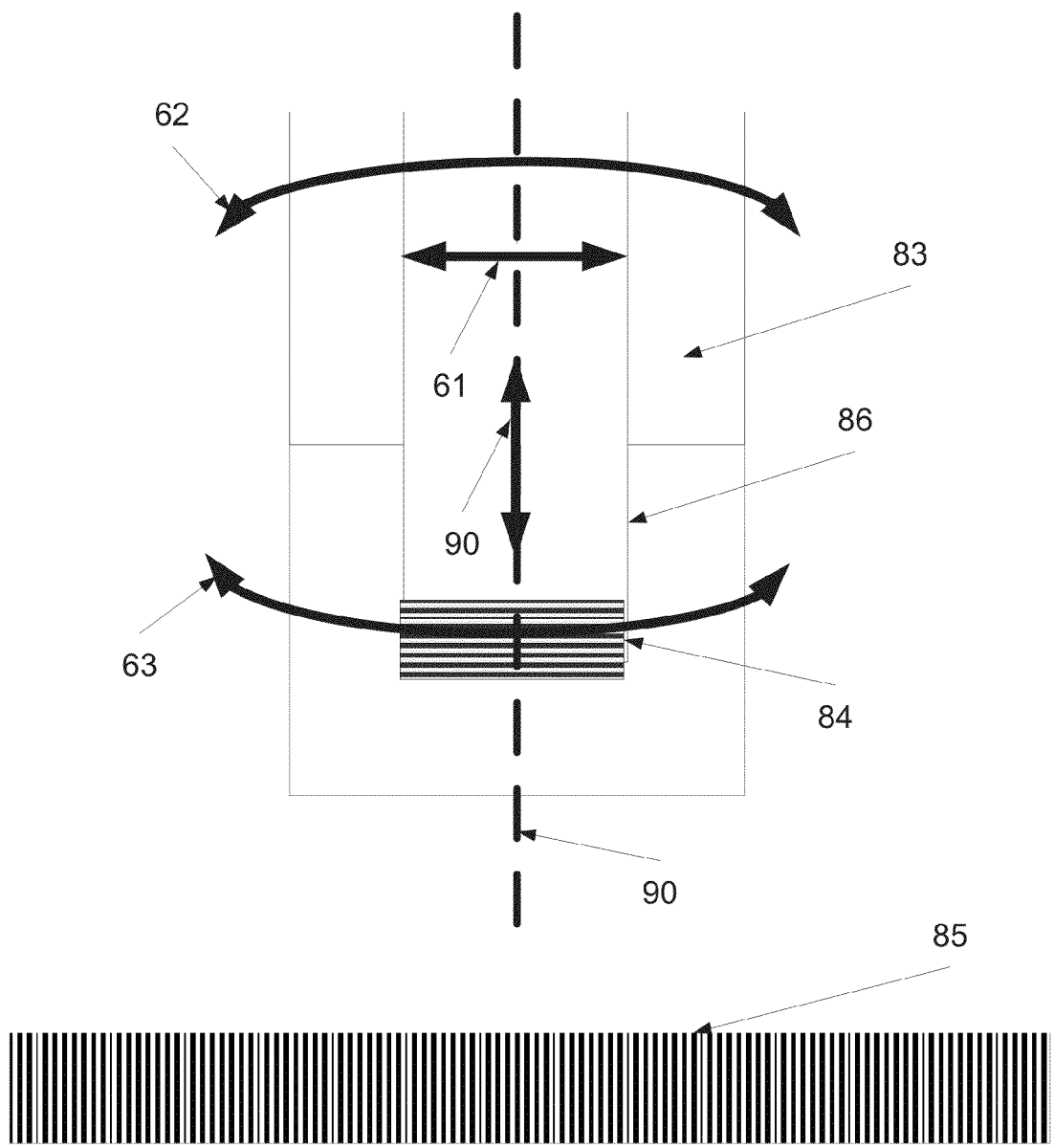
FIG. 3 is a lateral view of a portion of an extendable detector arm, such as depicted in FIG. 1, along an axis that is perpendicular to the longitudinal axis of the patient bed 85, according to some embodiments of the present invention.

Reference is now also made to FIG. 3, which is a lateral view of an extendable detector arm, such as 83 in FIG. 1, along an axis that is perpendicular to the longitudinal axis of the patient surface 85, according to some embodiments of the present invention. Optionally, as shown at FIG. 2A, the extendable detector arm 83 moves along the longitudinal axis of the patient surface 85, for example along the axis depicted in 61, or swings so that the tip of the extendable detector arm 83 scans the longitudinal axis of the patient surface 85, for example swings along a swing axis depicted in 62 or 63. Optionally, the extendable detector arm 83 is biased in an angle of about 2, 4, 5, 8, 10, 15, 30 degrees or any intimidate or higher degree in relation to a plane traversing the supporting framework 80, creating lateral translations of 1, 2, 5, 10 mm and/or greater, such as 2-25 cm or more, for example, 3, 4, 5, 8, 12, and the like).

The movement of the extendable detector arm 83 is optionally defined by a path, such as a groove, in the gantry 80 and controlled by the controller 82, for example according to a volumetric scanning pattern calculated and/or controlled by the scanning computing unit 87. Optionally, one or more motors actuate the swing of the extendable detector arm 83 and/or the movement thereof along the longitudinal axis of the patient surface 85 according to the outputs of the controller 82.

Optionally, some or all of the extendable detector arms 83 are rotated around their own axes, for example along the vector shown at 154. Optionally, the rotation is controlled by the controller 82, for example according to a volumetric scanning pattern calculated and/or controlled by the scanning computing unit 87.

Figure 4:
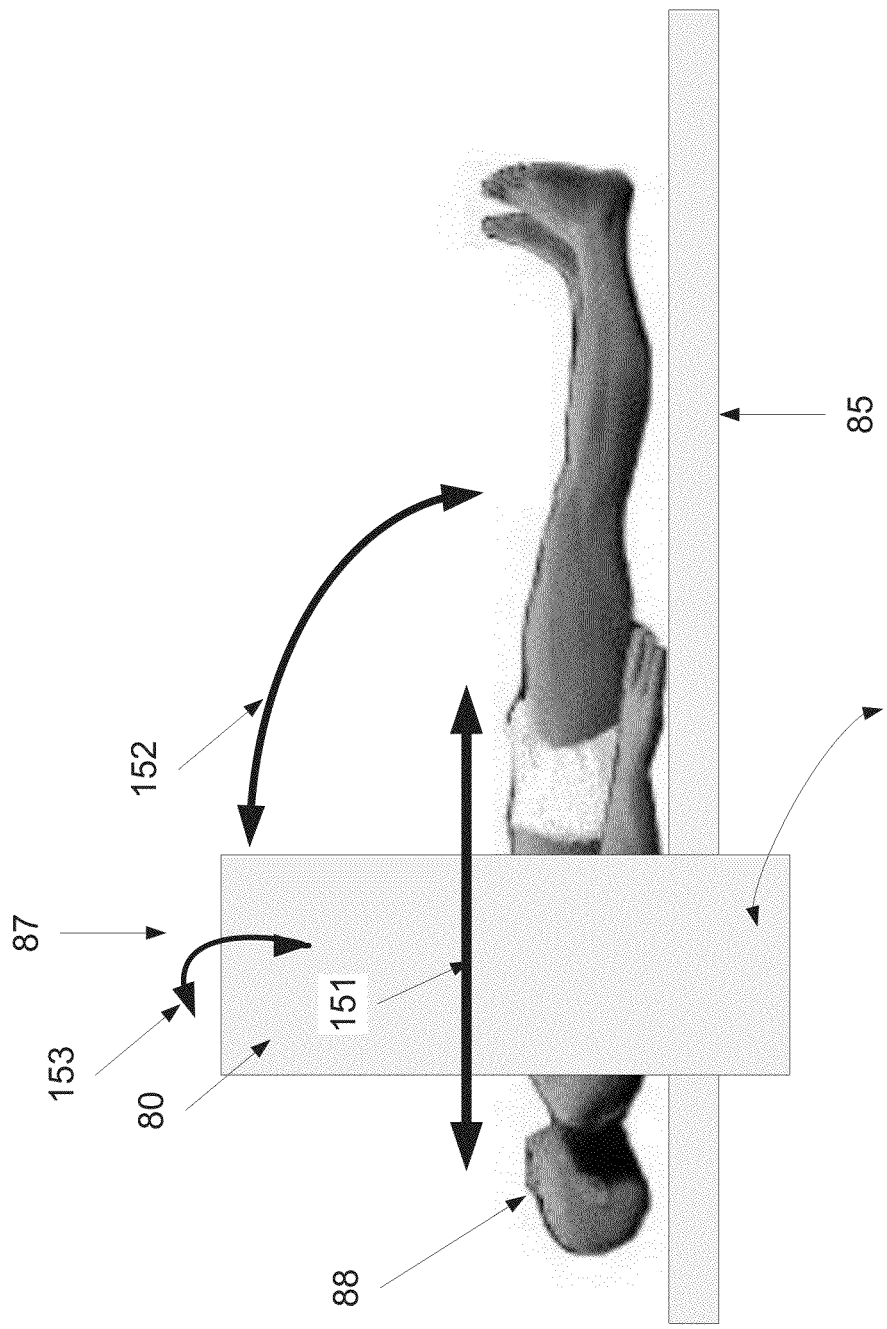
FIG. 4 is a lateral schematic illustration of an exemplary gantry and a patient horizontally positioned on a patient bed, according to some embodiments of the present invention.

Reference is now made to FIG. 4, which is a lateral schematic illustration of an exemplary gantry, such as 80, and a patient surface, such as 85, according to some embodiments of the present invention. FIG. 4 depicts optionally motion vectors of the gantry 80. The gantry 80 may be designed to move along these motion vectors during a scanning process, for example according to a volumetric scanning pattern calculated and/or controlled by the scanning computing unit 87. Optionally, one or more motors are connected to the gantry 80 to facilitate the movement thereof along these vectors. Optionally, the gantry 80 moves along the patient surface 85, for example along the vector shown at 151. Optionally, the gantry 80 tilted about an axis perpendicular to the longitudinal axis of the patient surface 85, for example along the vector shown at 152. Optionally, the gantry 80 rotates around a longitudinal axis of the patient surface 85, for example along the vector shown at 153. Optionally, the patient surface 85 moves through the gantry 80.

Figure 5B:
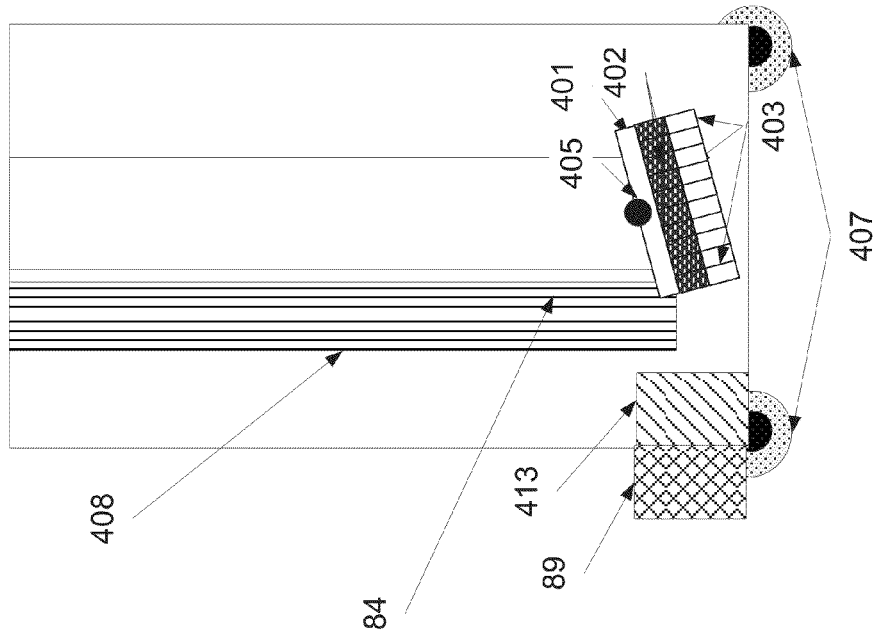
FIG. 5B is a sectional schematic illustration of the exemplary detection unit in the tip of an extendable detector arm of FIG. 5A a set of rollers are mounted on the tip, according to some embodiments of the present invention.
Figure 5A:
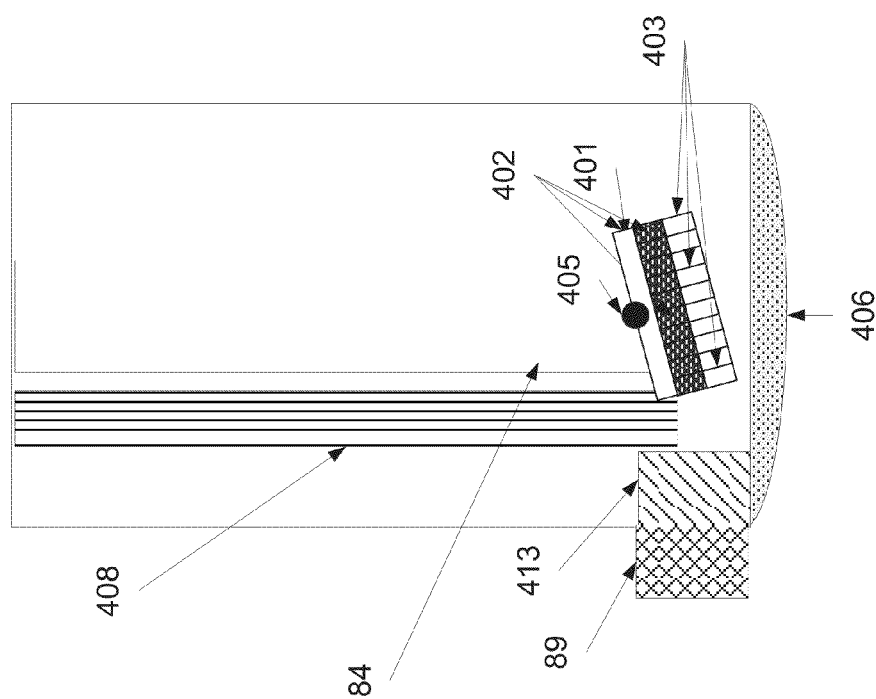
FIG. 5A is a sectional schematic illustration of an exemplary detection unit in a tip of an extendable detector arm, according to some embodiments of the present invention.

Reference is now made to FIG. 5, which is a sectional schematic illustration of an exemplary detection unit 84 in a tip of an extendable detector arm 83, according to some embodiments of the present invention. As shown at FIG. 5, the detection unit 84 includes a tilting mechanism 401 for tilting one or more radiation detectors such as semiconductor radiation detectors 402. The tilting mechanism 401 optionally includes a mount to which the radiation detectors 402 are connected. This tilting motion allows the semiconductor radiation detectors to scan a portion of the patient 88 in sweep motions, for example as described in International Application No. IL2005/001173, filed Nov. 19, 2005, which is incorporated herein by reference. Optionally, the semiconductor radiation detectors 402 sweep among a number of positions. Optionally, the angular deviation between the different positions is about ¼, ⅓, ½ and/or 1 degree. Optionally, the positions are spread over an angular opening of between about 10 and 120 degrees. Optionally, the angular opening and/or number of positions depend on the ROI, creating for example 10, 20, 30, 50, 100, 200, 500 or any intermediate or smaller number of positions for each radiation detector 402 which sweeps in a scan pattern. Optionally, the radiation detector 402 remains in each angular position for a time period of about 0.1 second, 0.2 second, 0.5 second, 0.8 second, 1 second, 1.5 second 3 sec, and 5 sec. Alternatively the radiation detector 402 sweeps in a continuous motion.

Optionally, the tilting mechanism 401 includes a mount hinged on a rotating shaft 405 and a motor for actuating the mount. The motor is optionally controlled by the controller 82. For example, the semiconductor radiation detectors 402 are 16×16 pixilated, 2.54×2.54 mm in size, CZT arrays. Optionally, the detector is fitted with a collimator, such as a parallel hole collimator 403. The collimator 403 defines the solid angle from which radioactive emission events may be detected. Optionally, different semiconductor radiation detectors 402 have collimators with different characteristics. In such an embodiment collimators of high and low resolutions may be combined. In such a manner, high and/or resolution images of the patient's body or any portion thereof may be taken using the volumetric scanner 81. Optionally, the length of the collimation size of the collimators is between about 2 cm and about 3 cm and their width is between about 2 mm and about 3 mm.

As described above, the extendable detector arm 83 has a proximity detector 89. Additionally or alternatively, the extendable detector arm 83 may further include one or more attenuation correction transducers 413, such as US transducers. Optionally, the ACSCs of each detection unit 84 is performed based on the output of an adjacent attenuation correction transducer 413 in the extendable detector arm 83, for example as described in U.S. Pat. No. 7,652,259, filed on Apr. 11, 2003, which is incorporated herein by reference. The ACSC allows correcting the effect of bodily movements, for example breathing motion.

Optionally, a pad 406, such as a gel pad, for example an ultrasonic coupling gel pad, is attached to the tip of the extendable detector arm 83 and/or to the size of the extendable detector arm 83. The pad protects the patient's skin from being abraded by the extendable detector arm 83 and optionally provides an ultrasonic coupling medium for the US transducers. Additionally or alternatively, as shown at FIG. 5B, one or more rollers 407, such as wheels or balls, are attached to the tip of the extendable detector arm 83. The rollers allow maintaining the tip of the extendable detector arm 83 close to the skin of the patient without rubbing so as to protect, or further protect, the patient's skin from being abraded by the extendable detector arm 83. The one or more rollers 407 also allow rotating the extendable detector arm 83 along the contour of the body of the patient 88 while the tip of the extendable detector arm 83 is in contact with the body of the patient 88.

According to some embodiments of the present invention, the volumetric scanner 87 includes a positioning unit which estimates the location of the patient before and/or during the scan. Optionally, the positioning unit includes one or more image sensors, such as one or more CCD cameras and an image processing module which estimates the contour of the body of the patient 88 according to an analysis of the output of the one or more CCD cameras and instructs the extendable detector arm 83 to follow a certain pattern according to the analysis. Optionally, the positioning unit includes one or more proximity sensors.

According to some embodiments of the present invention, some or all of the extendable detector arms 83 includes an X-ray source 408, such as a calibrated or uncalibrated solid radioactive source, an X-ray tube, for example a commercially available tungsten tube, and an anode tube. In such an embodiment, the detection unit 84 may be used for capturing both X-rays emitted from the X-ray source and Gamma ray from the body of the patient, for example from radioactive tracer material, also known as radiopharmaceuticals. In such an embodiment, the acquired X-ray and Gamma ray projections, optionally from detection units 84 in multiple extendable detector arm 83 are used to reconstruct an image, such as a 3D image or a 4D Image, for example by applying known tomographic reconstruction algorithms. This image may then be manipulated to show thin slices along any chosen axis of the body, similar to those obtained from other tomographic techniques, such as MRI, CT, and PET. Optionally, the X-rays and the Gamma ray are captured in different radiation interception sessions. In a first group of radiation interception sessions Gamma-rays are captured and the X-ray source is idle. In a second group of radiation interception sessions X-rays which are emitted from the X-ray source are captured. The time taken to obtain the X-ray and Gamma ray projection of in each angle and/or session may be variable, for example 2 minutes per session. Optionally, the X-Ray flux generated by the X-ray source is adapted to allow the detectors of the detection units 84 to function both as SPECT detectors and CT detectors. In such embodiments the X-Ray flux allows the detectors to perform photon counting, for example at a rate of 80,000 counts per second.

By using X-ray source, the volumetric scanner 81 may be used for computerized tomography (CT). As the detection units 84 and the X-ray source 408 are placed in proximity to the body of the patient 88, the effect of bodily movements has less affect on the reconstructed image. Moreover, the force applied by the plurality of extendable detector arms 83 holds, or sustainably holds the body of the patient 88 in place and limits its movement space. In such a manner, the patient moment has less effect on the reconstructed image. In such embodiments, the period of each scanning session, in which a slice is scanned, is set so that the time spent for scanning each slice is roughly equivalent for reconstructing a CT and SPECT images. Optionally X-ray projections are used for attenuation and/or scatter corrections of Gamma ray projections and vice versa.

Optionally, the CT to SPECT information is used in real time (one affect the scan of the other during the acquisition.

Optionally, the X-Ray source allows acquiring volumetric images by when extremely low dose are used. These images may have low resolution and therefore may be used for general anatomy/body contouring/motion correction, for example breathing correction, gating and the like.

Reference is now made to FIG. 6A, which is a schematic illustration of an arrangement which includes a CT scanner 251, as known in the art, and the volumetric scanner 81 which is placed abject thereto, for example as depicted in FIG. 1, according to some embodiments of the present invention. In such an embodiment, the patient 88 may be simultaneously imaged using by the CT scanner 251 and the volumetric scanner 81. Optionally, the scanning period of the CT scanner 251 and the volumetric scanner 81 is similar, for example about 2 minutes.

Figure 8:
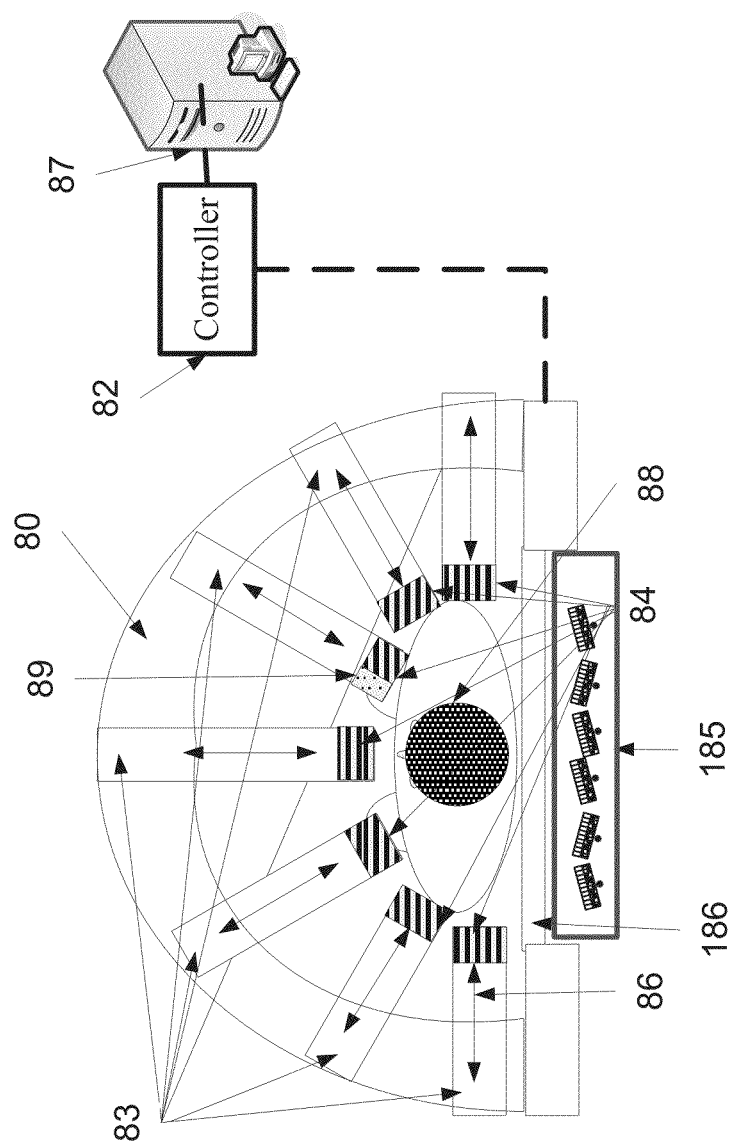
FIG. 8 is a sectional schematic illustration of a volumetric scanner as depicted in FIG. 1 with a patient bed as depicted in FIG. 7, according to some embodiments of the present invention.

Reference is now made to FIG. 7, which is a sectional schematic illustration of an exemplary back surface 185, along its latitudinal axis, according to some embodiments of the present invention. Optionally, the back surface 185, which I optionally placed below a pad 186 for lie on, allows capturing a Clinically-Valuable Image of the patient, for example as defined below. The exemplary back surface 185 includes a plurality of detection units 501. Optionally, each detection units as defined above, for example in relation to FIG. 5. Each one of the detection units 501 is connected to a controller and designed to capture X-ray and/or Gamma ray projections. Optionally, the patient surface 185 is the surface on which the patient lies. Optionally, as shown at FIG. 8, the back surface 185 is combined with the volumetric scanner 81 described in FIG. 1. In such an embodiment, the detection units 501 which are embedding in the back surface 185 are used to capture projection from the back side of the patient 88, facilitating a more robust reconstruction of the patient body and/or the patient's back. Optionally, in use, the bed is moved with the patient in and out of one or more gantries which support the aforementioned radiation detectors. In such an embodiment, the back surface 185 may remain in place while the bed moves.

Optionally, the detection units 501 are connected to one or more motors that allow changing their position in relation to the patient. In such a manner, the detection units 501 may be redistributed in the back surface 185 or therebehind after the patient is positioned horizontally thereon. Optionally, the detection units 501 are connected controlled according to the outputs of the controller 82, for example according to a volumetric scanning pattern defined by the scanning computing unit 87.

Figure 9:
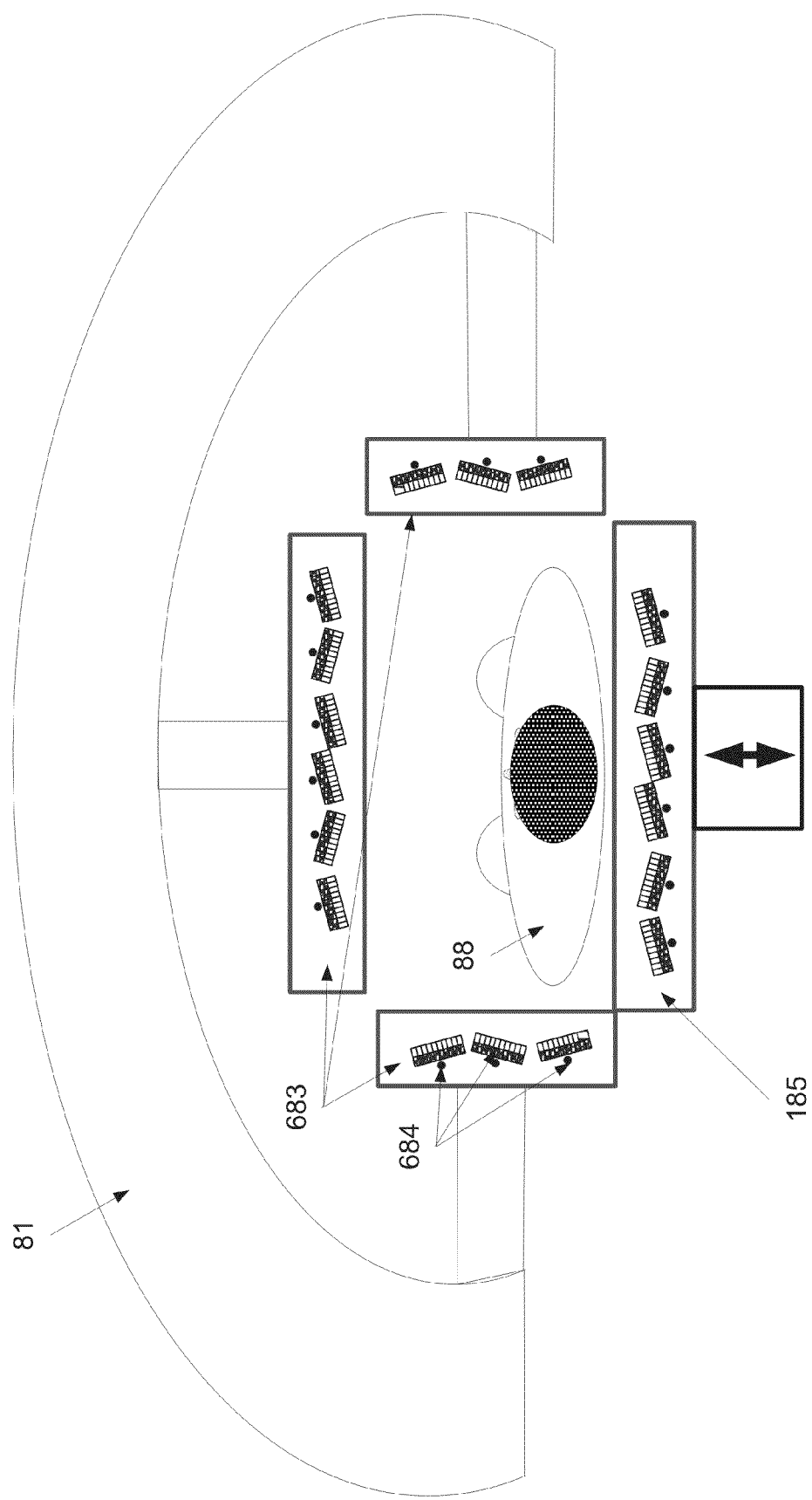
FIG. 9 is a schematic illustration a volumetric scanner having a plurality of extendable detector arms each with a plurality of detection units, according to some embodiments of the present invention.

Reference is now made to FIG. 9, which is a schematic illustration a volumetric scanner 81 having a plurality of extendable detector arms 683 each with a plurality of detection units, for example as shown at 684, according to some embodiments of the present invention. In this embodiment three extendable detector arms 683 are used for covering the patient's body together with the exemplary back surface 185 depicted in FIG. 7, each from a different side. Optionally, only the front extendable detector arm 683 has a plurality of detection units 684. Optionally, the volumetric scanner 81 allows capturing a Clinically-Valuable Image of the patient, as defined below.

According to some embodiments of the present invention, the number of extendable detector arms 83, which are used during a scan, is determined according to the shape and/or dimension of the patient's body and/or the organ which is about to be scanned, for example according to an estimation of the perimeter of patient at the axial plane which is about to be scanned. Optionally, the estimation is made using image processing techniques, for example by analyzing an image of the patient captured by an image detector and/or according to the outputs of some or all of the proximity detectors. For example, four extendable detector arms 83 may be used for imaging a body of a child, a thin patient, and/or a limb of the patient, and six extendable detector arms 83 may be used for imaging a body of an obese patient. In another example, four extendable detector arms 83 may be used for imaging the brain of a patient, creating a cerebral volumetric image, for example as shown in FIG. 2D, and six extendable detector arms 83 may be used for imaging the thorax of the patient.

According to some embodiments of the present invention, the radiation detectors of the detection unit 84 are set work both in a photon counting mode and in a flux measurement mode. Optionally, the detection unit 84 changes its working mode intermediately or sequentially. For example, one or more of the detection units 84 may be set to intermittently intercept Gamma radiation emitted from Tc99m at between about 130 Kilo electronvolt (KeV) and about 150 KeV and X-ray radiation from the body of the patient 88 at about 200 KeV. In such a manner, an energy window of between about 150 KeV and about 250 KeV may be used for detecting X-ray photons and separated them from Gamma ray photons. As such photons include relatively low scattering, the quality of the X-ray based image is relatively high. Optionally, the modes change every second such that in one second X-ray is intercepted and evaluated and in the following Gamma-ray is intercepted and evaluated. Optionally, a number of X-ray transmissions are performed in each X-ray session, optionally one every 0.1 second.

Optionally, the radiation detectors are optimized to measure the total flux of photons rather than being optimized for short acquisition with high flux of photons where each photon is characterized. In such embodiments, scatter affects the image. Optionally, the overall NM acquisition time is reduced to a scale of between about 1 minute and about 2 minutes for a certain region or less. In such a manner, the accuracy of the image registration may be increased, the number of used detectors may be reduced. By selecting an energy window, as described above, and checking it for each photon, photons may be filtered with high probability of being scattered from a lateral origin.

It should be noted that when the intercepted radiation is X-ray radiation, the X-ray source may be as depicted in numeral 408 of FIG. 5 and/or from an X-ray source placed in the gantry, for example as shown in FIG. 6B. The detection units may be activated in any of the aforementioned modes, separately and/or jointly, in any stage.

According to some embodiments of the present invention, a number scanning sessions are performed by the extendable detector arms 83. In such an embodiment, a group of extendable detector arms 83 is used to image the body of the patient 88 in a number of consecutive sessions. In each consecutive session other portions of the patient's body are scanned. In such an embodiment, patients in various sizes may be scanned using a limited number of extendable detector arms 83. For example, four extendable detector arms 83 may be used for imaging a body of a child, a thin patient, and/or a limb of the patient in a single session and a body of an obese patient in two or three sessions. Though this process may increase the time it takes to scan an obese patient, it allows using a device with less extendable detector arms 83.

According to some embodiments of the present invention, the back surface 185, or any other surface on which the patient is placed, is set to be vertically actuated, brings the patient's body closer to the detection units 84, for example to the tips of the extendable detector arms 83.

Figure 10:
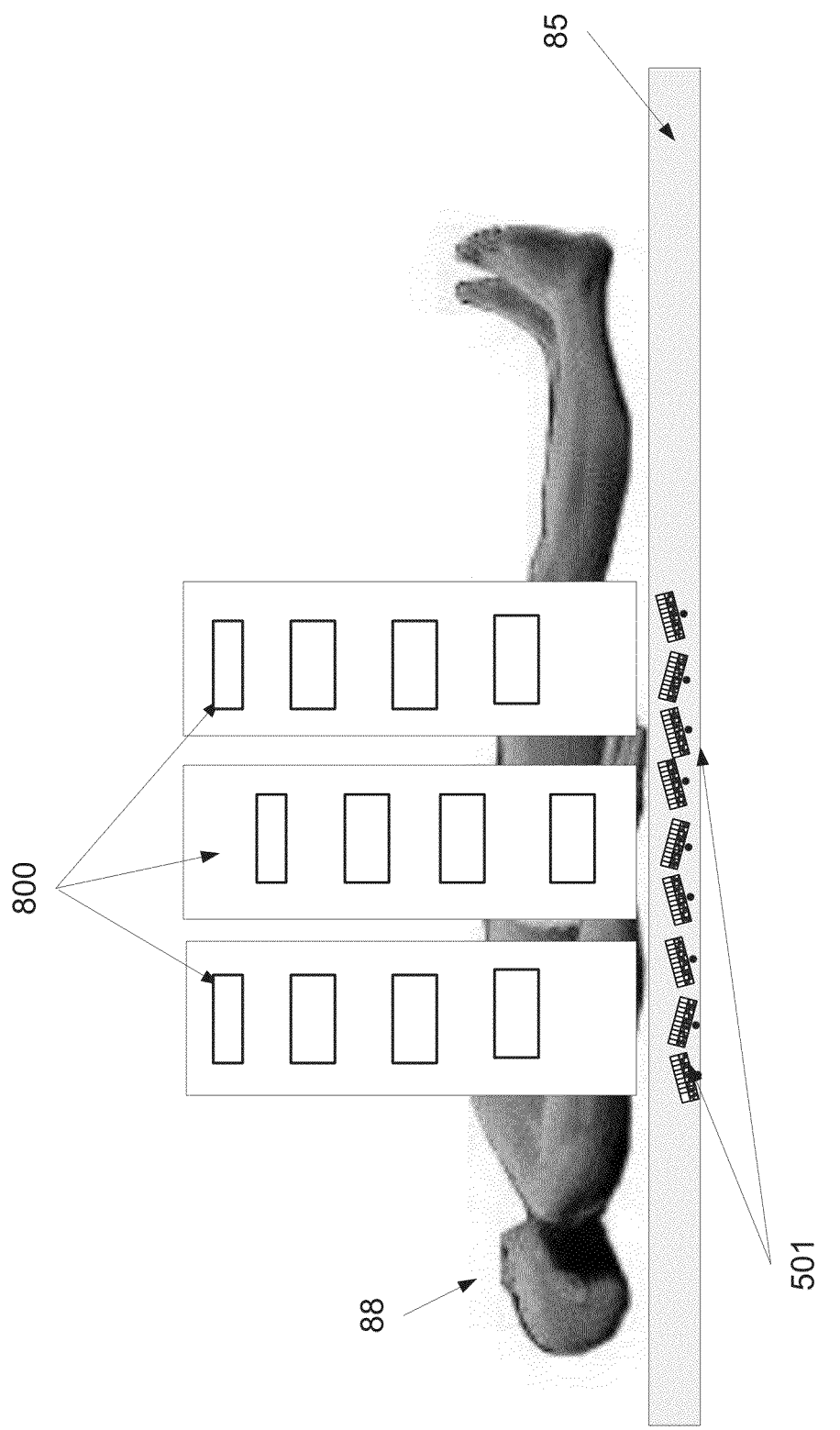
FIG. 10 is a schematic illustration of a volumetric scanner having a plurality of gantries, according to some embodiments of the present invention.

Reference is now also made to FIG. 10, which is a schematic illustration of a volumetric scanner 81 having a plurality of gantries 800, each optionally defined as gantry 80 of FIG. 1, according to some embodiments of the present invention. Optionally, the number of used gantries 800 is determined according the shape and/or dimension of the patient's body, for example according to an estimation of the perimeter of patient. For example, a single gantry 800 is used for imaging a body of a child, a thin patient, and/or a limb of the patient, and two or more gantries 800 may be used for imaging a body of an obese patient. Optionally, the gantries 800 are used for imaging parallel portions of the patient's body 88. Optionally, the extendable detector arms 83 of different gantries 800 are tilted to image a common portion of the patient's body 88. In such an embodiment the tip of the extendable detector arms 83 may intertwine along a common plane when they are extended to by in touch with the patient's body. For example, extendable detector arms 83 of a first gantry may be from two sides of an extendable detector arm of a second gantry. Optionally, each one of the gantries 800 is synchronized with one or more detection units 501 which are embedded in the patient surface, for example mounted in a surface below a mattress of a patient bed, for example as shown in FIG. 7.

The extendable detector arms 83 allow directing the detection units 84 to face different areas of the patient surface. Rather than facing the geometrical center of a space that is bounded by the gantry 80, the detection units 84 may be directed to face a selected region of interest which is outside of the bounded space.

Figure 11:
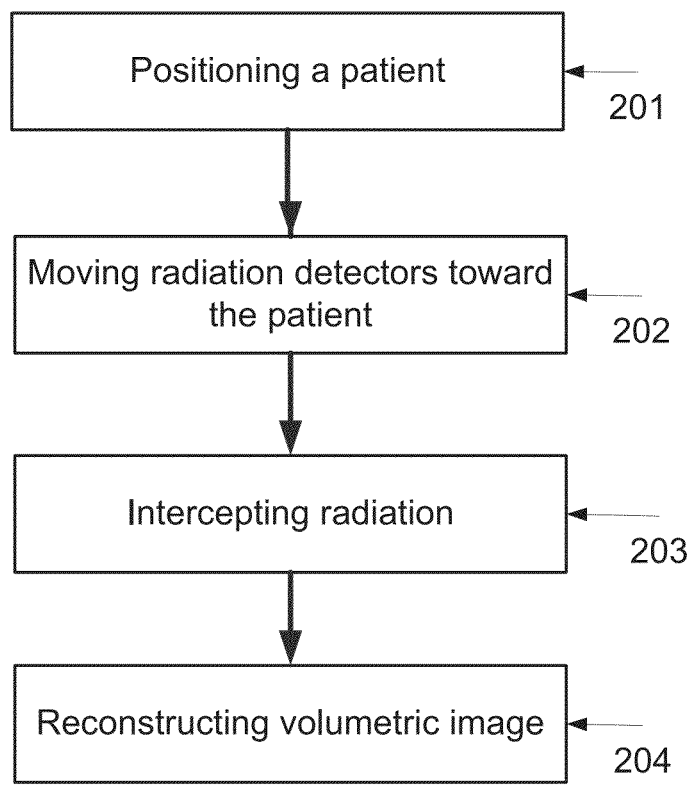
FIG. 11 is a flowchart of a method of performing a volumetric scan, according to some embodiments of the present invention.

Reference is now also made to FIG. 11, which is a flowchart of a method of performing a volumetric scan 200, according to some embodiments of the present invention. Optionally, the volumetric scan allows capturing a Clinically-Valuable Image of the patient, as defined below. First, as shown at 201 a surface of positioning a patient in a space parallel thereto is provided, for example the patient surface 85. In use, the patient lies down on the patient surface 85. Then, as shown at 202, a plurality of radiation detectors, such as the detectors in the detection units 84, are linearly extended toward a plurality of points of contact on the body of the patient and/or a plurality of points of proximity in relation to the body of the patient, for example by the extending of the linear actuators 86 from a plurality of distinct locations around the surface 85, on a framework, such as the gantry 80. Optionally, a point of proximity is defined a location from which the distance to the body of the patient is less than 5 cm, for example 1 cm, optionally 0.

Optionally, these distinct locations are apart from one another, for example 5 centimeter (cm) apart from one another, 10 cm apart from one another, 15 cm apart from one another or any intermediate or greater distance. Optionally, the extending length and/or angle of the extendable detector arms 83 is set according to a volumetric scanning pattern, for example controlled according to the controller 92 as defined above. Now, as shown at 203, radiation from the patient is intercepted by the plurality of radiation detectors. The radiation may be gamma ray and/or X-ray radiation, for example as outlined above. This allows, as shown at 204 reconstructing a volumetric image of one or more parts of the patient's body, for example using known SPECT, PET and/or CT imaging reconstruction techniques, for example as described in International Application No. IL2005/001173, filed Nov. 19, 2005, which is incorporated herein by reference.

Figure 12:
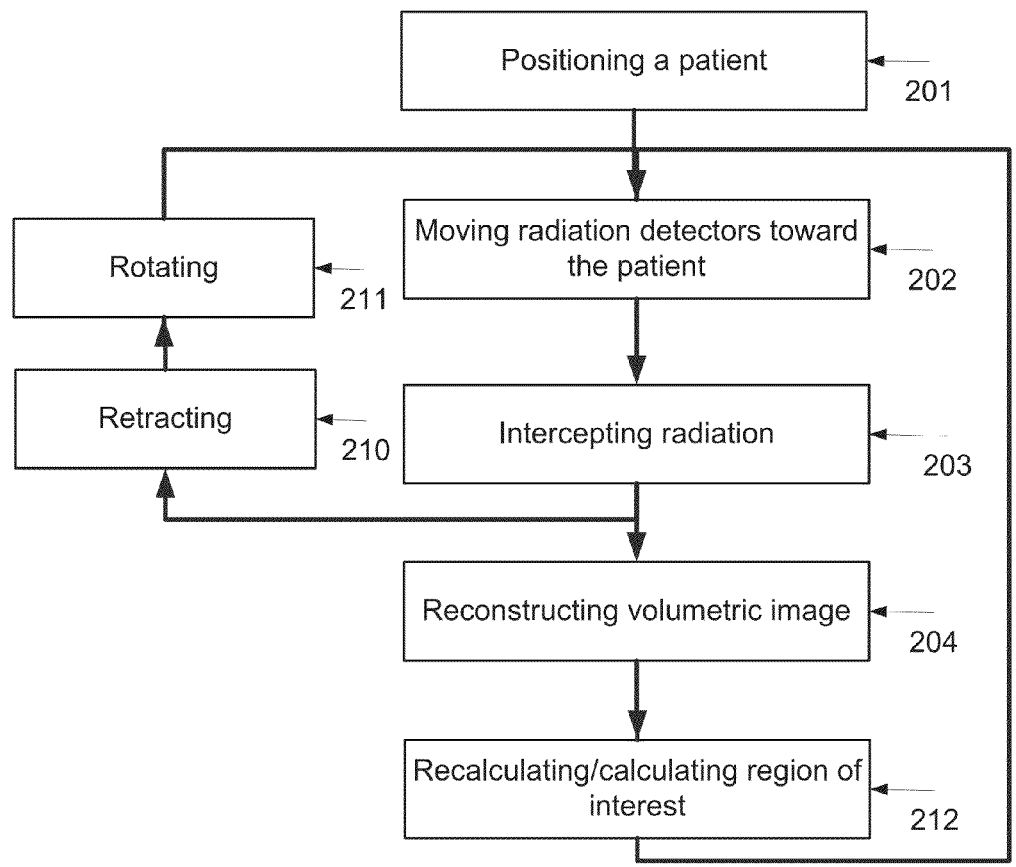
FIG. 12 is another flowchart of a method of performing a volumetric scan, according to some embodiments of the present invention.

FIG. 12 is another flowchart of a method of performing a volumetric scan, according to some embodiments of the present. Blocks 201-204 are as depicted in FIG. 11, however FIG. 12 further depicts blocks 210 and 211 in which the detection units 84 are optionally pulled from the points of contact and/or points of proximity and rotated to allow repeating 202-203 from other points of contact and/or points of proximity. The rotation may be performed by rotating the gantry 80 on which the detection units 84 are mounted. Optionally, the volumetric scan allows capturing a Clinically-Valuable Image of the patient, as defined below.

Optionally, as shown at 212, a region of interest is calculated, or recalculated, according to data in the image reconstructed in 211. In such an embodiment, the orientation of the extendable detector arms 83 and/or emission of the X-ray source 408 of some or all of them may be changed according to data in the image reconstructed in 211, for example a characteristic of pathological pattern. The orientation and/or emission of the detectors may be adjusted according to the new region of interest, for example to optimize the scan thereof. This process may be iteratively repeated, concentrating the imaging effort in the changing region of interest.

Optionally, the volumetric scanning pattern is adapted according to data that is captured and analyzed during the scan. In such an embodiment, suspected pathological sites may be detected by analyzing images which are substantially constantly reconstructed during the scan. These images, which are reconstructed based on a limited scanning data, allow capturing an image of a region of interest, which optionally includes a suspected pathological site that is indicative of abnormal cellular composition, cellular growth, fractures, lesions, tumors, hematomas and the like.

Additionally or alternatively, the scanning is adapted to focus on a predefined region of interest. Optionally, predefined region of interest is defined automatically and/or manually according to medical information that is received about the patient, for example similarly to the described in International Patent Application Publication No. WO2008/075362 published on Jan. 26, 2008, which is incorporated herein by reference. As used herein, medical information means, inter alia, information which is related to the patient, such as laboratory results, therapeutic procedure records, clinical evaluations, age, gender, medical condition, ID, genetic information, patient medical record, data indicating of metabolism, blood pressure, patient history, sensitivities, allergies, different population records, treatment methods and the outcome thereof, epidemiologic classification, and patient history, such as treatment history. In such embodiments, the orientation of the directable detectors may be changed in a manner that they are facing toward a region of interest of the patient, for example a known location of a tumor and/or a fracture. The coordinates of the location may be gathered by analyzing the medical information, for example using image processing techniques and/or manually inputted by the system operator and/or caretaker.

Additionally or alternatively, the intensity of the radiation that is emitted by the X-ray source 408 may be changed for example reduced and/or intensified during the volumetric scan. In such a manner, the radiation dose per volumetric scan may be reduced. The emission change reduces the total amount of the radiation that is absorbed by the patient and/or allows avoiding some or all of the redundant emissions. For example, instead of creating a high resolution volumetric CT image of the torso by irradiating the patient, from a plurality of angles, with fluxes which are high enough to overcome all the possible obstacles, for example ribs, initial scanning sessions and/or received medical information are used for identifying these obstacles so as to reduce the emission in areas in which they are present. Then, sideway views, optionally unradial, are taken to complete the missing data. In such a manner, data from a low-flux beam that would go radially towards the obstacle is compensated by either temporarily increasing the flux in an unblocked area and/or by taking additional side views that pass toward the region of interest.

According to some embodiments of the present invention, the orientation of the extendable detector arms 83 and/or emission of the X-ray source 408 of some or all of them may be changed according to characteristics of the region of interest and/or the location thereof. The characteristics can affect area to be scanned, for example the scanning speed, the contrast martial flux and/or wait time, the estimated scatter, attenuation, and/or resolution and the like. All these may be automated for that purpose, save time, and improve quality. The orientation and/or emission of the detectors may be adjusted according to characteristics of a suspected abnormality and thus optimizing the actual scan of the region of interest. For example, a change in an estimated anatomy, physiology, and/or metabolism may be detected during the performance of the scan and taken into account. The orientation and/or emission of the detectors may be changed to acquire more data pertaining to the region of interest and/or the specific suspected pathological sites.

According to some embodiments of the present invention, the orientation of the extendable detector arms 83 and/or emission of the X-ray source 408 of some or all of them may be changed so as to reduce the radiation that is transmitted via and/or toward radiation sensitive areas, such as the gonads, the eyes, the spinal cord, the salivary glands and/or breasts. In such an embodiment, the radiation sensitive areas are detected either in advance or in the initial scanning sessions. Then, the detectors are directed to avoid transmitting radiation toward the radiation sensitive areas and/or to reduce the intensity of the emission transmitted toward the radiation sensitive areas.

In such an embodiment, the detection units 84, and their radiation, are primarily focused on the region of interest. In such a manner, the focusing on one or more regions of interest may continuously improved, allowing focusing the resources on an area that matters the most for the diagnosis of the medical condition of the patient.

Definition of a Clinically-Valuable Image

In consequence to the features described above, the volumetric scanner 81 is capable of producing a "clinically-valuable image" of an intra-body region of interest (ROI) to containing a radiopharmaceutical, while fulfilling one or more of the following criteria:

1. the volumetric scanner 81 is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the volumetric scanner 81 is capable of acquiring at least one of 2000 photons emitted from the ROI during the image acquisition procedure;
2. the volumetric scanner 81 is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment, the volumetric scanner 81 is capable of acquiring at least 1,000,000 photons emitted from a volume of the ROI having a volume of no more than 200 cc;
3. the volumetric scanner 81 is capable of acquiring an image of a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to $10^5$ photons/second/cc, such that the range I is 105 photons/second/cc, and at least 50% of the voxels of the reconstructed three-dimensional intensity image of the ROI have inaccuracies of less than 15% of range I, i.e., less than $1.5\times10^4$ photons/second/cc. For some applications, the study produce a parametric image related to a physiological process occurring in each voxel. In one particular embodiment, the image has a resolution of at least 5×5×5 mm, and at least 50% of the voxels have inaccuracies of less than 15% of range I;
4. the volumetric scanner 81 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the radiopharmaceutical as distributed within the ROI has a range of emission-intensities I (which is measured as emitted photons/unit time/volume), and wherein at least 50% of the voxels of the reconstructed three-dimensional emission-intensity image of the ROI have inaccuracies of less than 30% of range I, such as less than 25%, 20%, 15%, 10%, 5%, 2%, 1%, or 0.5% of range I. For example, the radiopharmaceutical may emit over a range from 0 photons/second/cc to 105 photons/second/cc, such that the range I is 105 photons/second/cc, and at least 50% of the voxels of the reconstructed three-dimensional intensity image of the ROI have inaccuracies of less than 15% of range I, i.e., less than $1.5\times10$ photons/second/cc. For some applications, the study produces a parametric image related to a physiological process occurring in each voxel. In one particular embodiment, the image has a resolution of at least 5×5×5 mm, and at least 50% of the voxels have inaccuracies of less than 15% of range I;
5. the volumetric scanner 81 is capable of acquiring an image, which has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values I, and wherein at least 50% of the voxels of the reconstructed parametric three-dimensional image have inaccuracies less than 100% of range I5 such as less than 70%, 50%, 40%, 30%, 25%, 20%, 15%, 10%, 5%, 2%, 1%, or 0.5% of range I. For example, the physiological process may include blood flow, the values of the parameters of the physiological process may have a range from 0 to 100 cc/minute, such that the range I is 100 cc/minute, and at least 50% of the voxels of the reconstructed parametric three-dimensional image have inaccuracies less than 25% of range I, i.e., less than 25 cc/minute. In one particular embodiment, the image has a resolution of at least 5×5×5 mm, and at least 50% of the voxels have inaccuracies of less than 25% of range I; and/or
6. the volumetric scanner 81 is capable of acquiring an image, which has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein if the radiopharmaceutical is" distributed substantially uniformly within a portion of the ROI with an emission-intensity I+/−10% (which is defined as emitted photons/unit time/volume), and wherein at least 85% of the voxels of the reconstructed three-dimensional emission-intensity image of the portion of the ROI have inaccuracies of less than 30% of intensity I, such as less than 15%, 10%, 5%, 2%, 1%, 0.5%, 20%, or 25% of intensity I. For example, the radiopharmaceutical may be distributed within a volume with a uniform emission-intensity I of $10^5$ photons/second/cc, and at least 85% of the voxels of the reconstructed three-dimensional intensity image of the volume have inaccuracies of less than 15% of intensity I, i.e., less than $1.5\times10^4$ photons/second/cc. For some applications, the same definition may apply to a study which produces a parametric image related to a physiological process occurring in each voxel. In one particular embodiment, the image has a resolution of at least 5×5×5 mm, and at least 50% of the voxels have inaccuracies of less than 15% of intensity I.

It is expected that during the life of a patent maturing from this application many relevant systems and methods will be developed and the scope of the term image, scanning, and directable detector is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for performing volumetric imaging of at least a portion of a patient's body, comprising:
    a) providing a system which comprises
        i) a surface for positioning at least a portion of said patient's body in a space adjacent thereto;
        ii) a plurality of extendable detector arms each having
            a) at least one detection unit which comprises at least one pixilated solid-state radiation detector and at least one collimator; and
            b) at least one actuator operable to move said detection unit; and
        iii) a gantry which supports said plurality of extendable detector arms; and
    b) using said system to image at least a portion of said patient's body by approaching only some of said detection units to relatively near said body and leaving others of said detection units relatively distant from said body while using said detection units to collect radiation data from said body.

2. The method of claim 1, wherein in at least one of said extendable arms comprises a plurality of actuators operable to move a same detection unit.

3. The method of claim 1, wherein at least one of said detector arms comprises a plurality of detection units.

4. The method of claim 1, wherein at least one of said at least one detection units comprises a plurality of pixilated solid state radiation detectors.

5. The method of claim 1, further comprising selecting detection units to be approached to said patient as a function of patient size.

6. The method of claim 1, further comprising selecting detection units to be approached to said patient as a function of size of a Region of Interest and as a function of shape of a body part of said patient which body part comprises said region of interest.

7. The method of claim 1, further comprising using data from said approached detection units to calculate a volumetric image.

8. The method of claim 1, further comprising using data from both said approached units and from said other units to calculate a volumetric image.

9. The method of claim 8, further comprising using data from detection units which are distant in a first phase of scanning, and using data from detection units which are approached to a patient in a second phase of scanning.

10. The method of claim 1, further comprising using data obtained from at least one of said detection units in a first phase of radiation detection to calculate a scanning pattern for at least one of said detector units during a second phase of scanning.

11. The method of claim 1, wherein said scanning comprises using at least one of said detector units which comprises a collimator having a first set of physical characteristics and using at least one of said detector units which comprises a collimator having a second set of physical characteristics.

12. The method of claim 11, comprising using detector units having said first set of characteristics prior to using detector units having said second set of characteristics.

13. The method of claim 11, comprising using said detector units having said first and second sets of characteristics when performing a same scan.

14. The method of claim 11, wherein said second of said sets of collimator characteristics defines a higher resolution than the resolution defined by said first set of collimator characteristics.

15. The method of claim 1, further comprising advancing at least one of said detector units until it is in contact with said body (clothed or unclothed), and displacing said detector along said body while said detector is in continuous contact with said body and is detecting radiation from said body.

16. A method for volumetric imaging comprising:
 a) providing a system which comprises
  i) a surface for positioning at least a portion of a patient's body in a space adjacent thereto;
  ii) a plurality of extendable detector arms each having at least one detection unit which comprises
   a) at least one pixilated solid-stated detector and at least one collimator; and
   b) at least one actuator operable to move said detection unit; and
  iii) a gantry which supports said plurality of extendable detector arms;
 b) positioning at least one of said detection units in proximity to a patient;
 c) operating said detectors to acquire date from said detection unit;
 d) calculating a desired scan pattern, said calculation being based at least in part on said acquired data;
 e) repositioning or reorienting at least one of said detector units according to said desired scan pattern; and
 f) using said repositioned or reoriented detector unit to acquire additional radiation detection data.

17. The method of claim 16, wherein at least one of said detector arms further comprises a plurality of detection units.

18. The method of claim 16, further comprising advancing at least one of said detector units until it is in contact with said body (clothed or unclothed), and displacing said detector along said body while said detector is in continuous contact with said body and is detecting radiation from said body.

19. A method for performing a volumetric scan which comprises
 a) providing a system which comprises
  i) a surface for positioning at least a portion of a patient's body in a space adjacent thereto;
  ii) a plurality of extendable detector arms each having
   a) at least one detection unit which comprises at least one pixilated solid-state detector and at least one collimator; and
   b) an actuator operable to move said detection unit; and
  iii) a gantry which supports said plurality of extendable detector arms,
 b) approaching at least one of said detection units towards the patient's body; and
 c) positioning at least one of said detection units at a plurality of positions and/or orientations while detecting radiation from at least a portion of a patient's body by at least one of a group consisting of
  i) rotating said gantry during said detecting process; and
  ii) at least partially rotating said at least one detection unit during said detecting process.

20. The method of claim 19, further comprising at least one of
 a) advancing said detection unit until it is in contact with a patient, and there detecting radiation; and
 b) positioning said detection unit at a distance from said body, and there at least partially rotating said detector unit during said detecting of radiation.

21. The method of claim 20, comprising advancing said detection unit until it is in contact with a patient, and there detecting radiation prior to positioning said detection unit at a distance from said body.

22. The method of claim 20, comprising positioning said detection unit at a distance from said body, and there at least partially rotating said detector unit during said detecting of radiation prior to advancing said detection unit until it is in contact with a patient.

23. The method of claim 19, wherein at least one of said detector arms comprises a plurality of detector units.

24. The method of claim 19, wherein at least one of said detector units comprises a plurality of pixilated solid-state detectors.

25. The method of claim 19, wherein at least one of said detector arms comprises a plurality of actuators operable to move a same detection unit.

* * * * *